(12) United States Patent
Eichen et al.

(10) Patent No.: US 9,518,964 B2
(45) Date of Patent: Dec. 13, 2016

(54) METHOD FOR IDENTIFYING ELECTROPHILES AND NUCLEOPHILES IN A SAMPLE

(76) Inventors: Yoav Eichen, Haifa (IL); Shay Tal, Kiryat-Motzkin (IL); Yael Abraham, Ashdod (IL); Husein Salman, Golan Heights (IL); Elana Borzin, Haifa (IL); Carmit Hertzog-Ronen, Kiryat-Motzkin (IL)

( * ) Notice: Subject to any disclaimer, the term of this patent is extended or adjusted under 35 U.S.C. 154(b) by 1442 days.

(21) Appl. No.: 13/086,486

(22) Filed: Apr. 14, 2011

(65) Prior Publication Data

US 2011/0281742 A1    Nov. 17, 2011

Related U.S. Application Data

(63) Continuation-in-part of application No. 12/320,777, filed on Feb. 4, 2009, now abandoned, and a continuation-in-part of application No. 12/087,235, filed as application No. PCT/IL2006/001503 on Dec. 28, 2006, now abandoned.

(30) Foreign Application Priority Data

Dec. 29, 2005   (IL) .......................................... 172902
Feb. 4, 2008   (IL) .......................................... 189253

(51) Int. Cl.
| | | |
|---|---|---|
| C40B 30/00 | (2006.01) | |
| C40B 40/00 | (2006.01) | |
| G01N 31/22 | (2006.01) | |
| G01N 33/00 | (2006.01) | |
| G01N 21/77 | (2006.01) | |
| G01N 21/64 | (2006.01) | |

(52) U.S. Cl.
CPC .......... *G01N 31/22* (2013.01); *G01N 33/0036* (2013.01); *G01N 33/0057* (2013.01); *G01N 31/223* (2013.01); *G01N 31/224* (2013.01); *G01N 2021/6439* (2013.01); *G01N 2021/773* (2013.01); *Y10T 436/23* (2015.01)

(58) Field of Classification Search
CPC .... G01N 31/22; G01N 31/223; G01N 31/224; G01N 33/0057; G01N 33/0036; G01N 2021/6439; G01N 2021/77; G01N 2021/773; Y10T 436/23
See application file for complete search history.

(56) References Cited

U.S. PATENT DOCUMENTS

| | | |
|---|---|---|
| 3,645,693 A | 2/1972 | Poziomek et al. |
| 5,846,836 A | 12/1998 | Mallow |
| 2005/0147534 A1 | 7/2005 | Swager et al. |

FOREIGN PATENT DOCUMENTS

| | | |
|---|---|---|
| EP | 0881225 A2 | 12/1998 |
| EP | 1081152 A1 | 3/2001 |
| WO | 2007074461 A1 | 7/2007 |
| WO | 2012005274 A1 | 1/2012 |

OTHER PUBLICATIONS

Peck, Konan et al. "Single-molecule fluorescense detection: autocorrelation criterion and experimental realization with phycoerythrin." PNAS USA (1989) 86 4087-4091.*
Callan et al: "Luminescent sensors and switches in the early 21st century" Tetrahedron, Elsevier Science Publishers, Amsterdam, NL, vol. 61, No. 36, Sep. 5, 2005, pp. 8551-8588.
ESR for corresponding EP09001453.1 mailed Aug. 17, 2009.
ISR for WO2007/074461 dated Apr. 27, 2007.
James K Tusa et al: "Critical care analyzer with fluorescent optical chemosensors for blood analytes" Journal of Materials Chemistry, The Royal Society of Chemistry, Cambridge, GB, vol. 15, May 13, 2005, pp. 2640-2647.
Mohr et al: "Covalent bond formation as an analytical tool to optically detect neutral and anionic analytes" Sensors and Actuators B, Elsevier Sequoia S.A., Lausanne, CH, vol. 107, No. 1, May 27, 2005, pp. 2-13.
Stitzel, Shannon E. et al: "Array-to-Array Transfer of an Artificial Nose Classifier" Analytical Chemistry, 2001, 73 (21), pp. 5266-5271.

\* cited by examiner

*Primary Examiner* — Christopher A Hixson
(74) *Attorney, Agent, or Firm* — Graeser Associates International Inc; Dvorah Graeser

(57) ABSTRACT

A method and device for identifying a molecule in a sample, the molecule comprising an electrophilic or nucleophilic moiety. The method comprises contacting the sample with a plurality of chemosensors, each of the chemosensors comprising a π-conjugated system and a moiety having a nucleophilic property or an electrophilic property; and measuring an electromagnetic property of each of the chemosensors in the sample; whereby the pattern of changes in the electromagnetic properties of the plurality of chemosensors after chemically reacting with the electrophile or nucleophile of the molecule identifies the molecule in said sample. The device comprises a substrate carrying a plurality of chemosensor molecules having at least one predetermined electromagnetic property, the at least one electromagnetic property being changeable by subjecting the chemosensor molecules to a sample containing at least one electrophile or nucleophile, wherein the pattern of change of the electromagnetic property of the plurality of chemosensor molecules allows the device to identify the electrophile or nucleophile in the sample.

36 Claims, 5 Drawing Sheets

METHOD FOR IDENTIFYING ELECTROPHILES AND NUCLEOPHILES IN A SAMPLE

RELATED APPLICATION

This application is a Continuation-in-Part of U.S. application Ser. No. 12/087,235, filed on Dec. 2, 2008, which claims priority from PCT Application No. PCT/IL2006/001503, filed on Dec. 28, 2006, which claims priority from Israeli Application No. 172902, filed on Dec. 29, 2005; and which is also a Continuation-in-Part of U.S. application Ser. No. 12/320,777, filed on Feb. 4, 2009, which claims priority from Israeli Application No. 189253, filed on Feb. 4, 2008; all of which are incorporated by reference as if fully set forth herein.

FIELD OF THE INVENTION

This invention relates generally to chemosensors for identifying electrophilic and nucleophilic molecules.

BACKGROUND OF THE INVENTION

Electrophiles such as dimethyl sulfate and alkyl halides and nucleophiles such as pyridine, amines and alcohols are commonly used in organic syntheses for research as well as for industrial purposes. Some of these agents, because of their alkylating power, are also being used as soil sterilizers, anticancer drugs and in a great variety of other applications.

Many of electrophilic materials, especially methylating agents, are toxic or mutagenic because of their ability to react with the many nucleophilic species in the animal body, e.g. DNA, thus introducing defects into the genetic code, which is associated with mutagenesis and carcinogenesis. Many nucleophilic materials, especially amines, are toxic and irritants because of their ability to react with different living tissues, inflicting severe damages to living organisms.

The combination of wide use and high toxicity of electrophiles and nucleophiles has presented a unique need for new, simple, sensitive and informative methods for their detection both in solution and in the gas phase. Attempts of various researchers to develop efficient sensing tools for electrophiles and nucleophiles focused mainly on colorimetric systems that change their color in the presence of an electrophile or nucleophile.

One method for the detection of alkylating agents which are electrophiles, such as nitrogen or sulfur mustards, is disclosed in International Publication No. WO 04/081561 [Ref. 1]. The disclosed method relates to mixing a sample solution suspected of containing a nitrogen or sulfur mustard with a reagent comprising 4-(4'-nitrobenzyl)pyridine or analogues thereof, and an additive selected from the group consisting of mercuric cyanide, a group I or group H metal perchlorate and mixtures thereof.

Yet another approach to the detection of such alkylating agents is the use of PET-based chemosensors. PET-based chemosensors consist of a luminescent species (e.g. a fluorophore) attached to a nucleophilic group. In the unbound state, the nucleophilic group quenches the excited state of the fluorophore, usually by its lone pair electrons of the unoccupied nucleophilic binding site. Upon binding an electrophile (such as a Lewis acid), the lone pair electrons of the binding group, which previously served as the quencher of the fluorophore of the PET system, is engaged in the newly formed bond. Consequently, this lone pair of electrons can no longer quench the fluorophore and the luminescence is regained, thus signaling the capture of Lewis acid.

The PET approach has been employed in various detection methods. Weller et al [Refs. 2 and 3] developed a method for reporting the presence of metal cations and protons using the Photo-induced Electron Transfer (PET) and/or Photo-Induced Energy Transfer (PEET or EET) signaling approaches.

US application No. 2005/147534 [Ref. 4] relates to a class of luminescent and conductive polymer compositions having chromophores exhibiting increased luminescent lifetimes, quantum yields and amplified emissions. This application further discloses a sensor and a method for sensing an analyte through the luminescent and conductive properties of the polymers. Such analytes include aromatics, phosphate ester groups and in particular explosives and chemical warfare agents in a gaseous state.

A plurality of chemosensors can identify electrophilic and nucleophilic molecules by chemically reacting with them. The reaction of each chemosensor with its target molecules results in the induction of a change in its electromagnetic properties. By assembling a plurality of different chemosensors or chemosensor combinations into a matrix of chemosensor sites one may obtain a plurality of reactions of different chemosensors with the detected molecule. The pattern of reaction-induced changes of the electromagnetic properties of the sensors can therefore identify the molecule.

Thus, the present invention provides methods for identifying electrophilic and nucleophilic molecules in a sample, the molecule includes at least one electrophilic or nucleophilic moiety. In one method, the sample is contacted with a plurality of chemosensors, each of the chemosensors having a π-conjugated system and a moiety having a nucleophilic property or an electrophilic property. At least one electromagnetic property of each of said chemosensors in the sample is measured. The pattern of changes in the electromagnetic properties of the plurality of chemosensors as a function of chemically reacting with said electrophile or nucleophile of said molecule can identify the molecule in the sample.

The present invention also provides a device for the identification of a molecule that is an electrophile or nucleophile. The device includes a substrate carrying a plurality of chemosensor molecules having at least one predetermined electromagnetic property.

The electromagnetic property can change by subjecting chemosensor molecules to a sample containing the molecule that is an electrophile or nucleophile under conditions in which the chemosensors react with them. The pattern of change of said electromagnetic property of said plurality of chemosensor molecules allows the device to identity of said electrophile or nucleophile in said sample.

chemosensor molecules to a sample containing the molecule that is an electrophile or nucleophile under conditions in which the chemosensors react with them. The pattern of change of said electromagnetic property of said plurality of chemosensor molecules allows the device to identity of said electrophile or nucleophile in said sample.

DESCRIPTION OF FIGURES

Figure 1A:
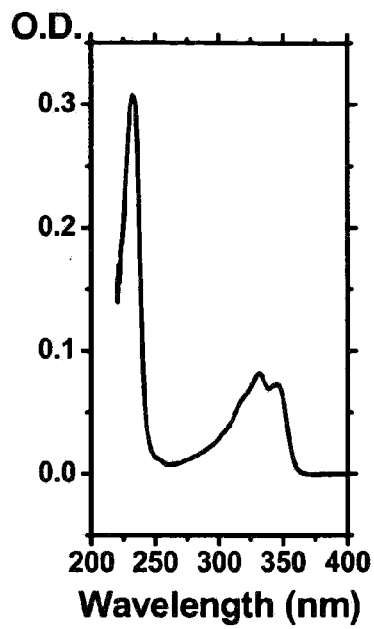
FIGS. 1A and 1B exhibit the absorption and luminescence spectra of compound 1 in the presence of an electrophile.
Figure 1B:
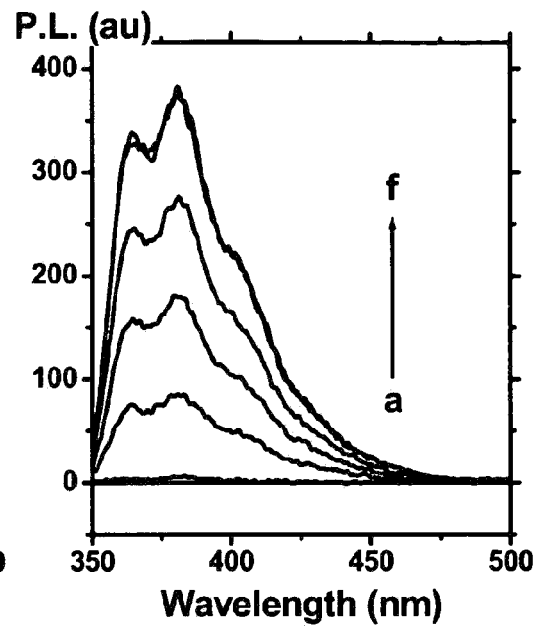

FIGS. 1A and 1B exhibit the absorption and luminescence spectra of compound 1 in the presence of an electrophile.

Figure 2:
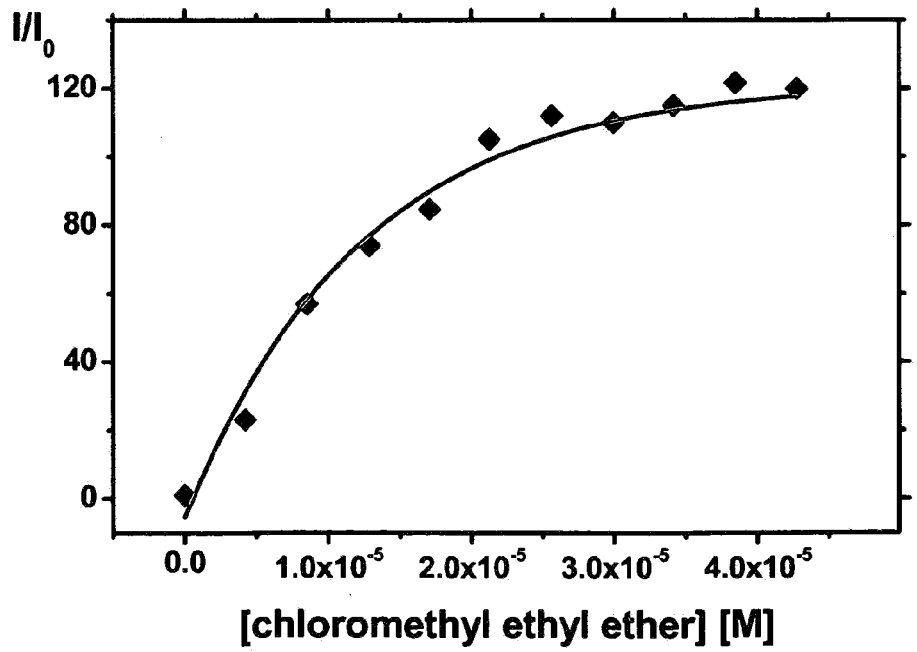
FIG. 2 shows the relative fluorescence intensity of a solution of 1 in acetonitrile ([1]=$2.2*10^{-5}$ M) as a function of the chloromethyl ethyl ether concentration.

FIG. 2 shows the relative fluorescence intensity of a solution of 1 in acetonitrile ($[1]=2.2*10^{-5}$ M) as a function of the chloromethyl ethyl ether concentration.

Figure 3:
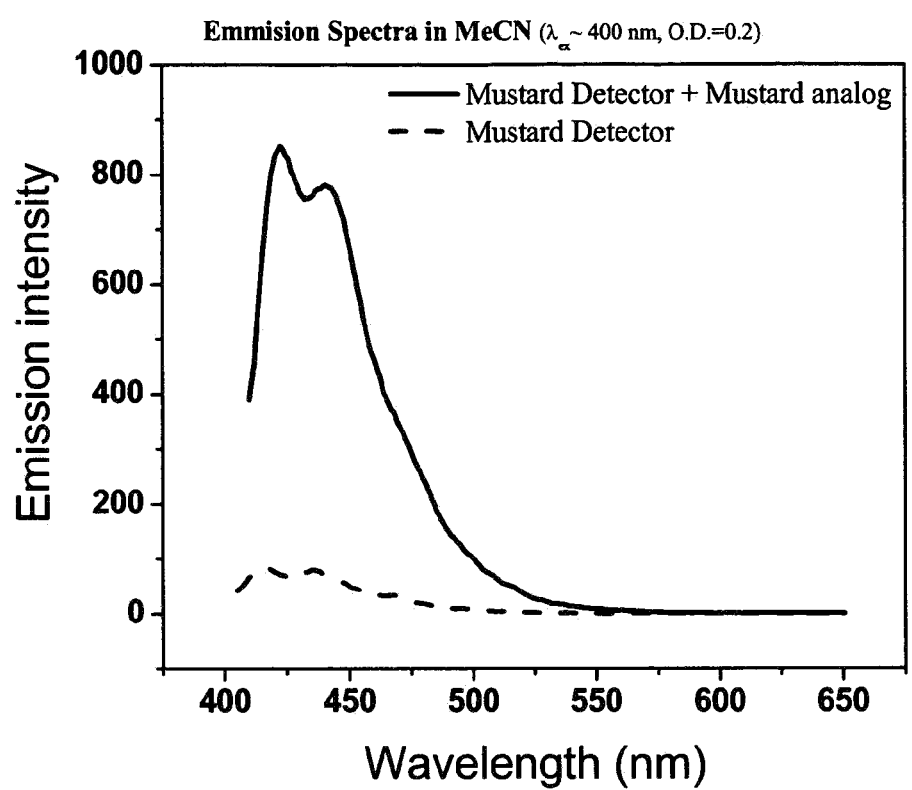

FIG. 3 shows the emission spectra of the chemosensor 4,6-dietoxy-1,8-naphthalimide before and after the interaction with the alkylating agent 2-chlorodiethylsulfide.

Figure 4:
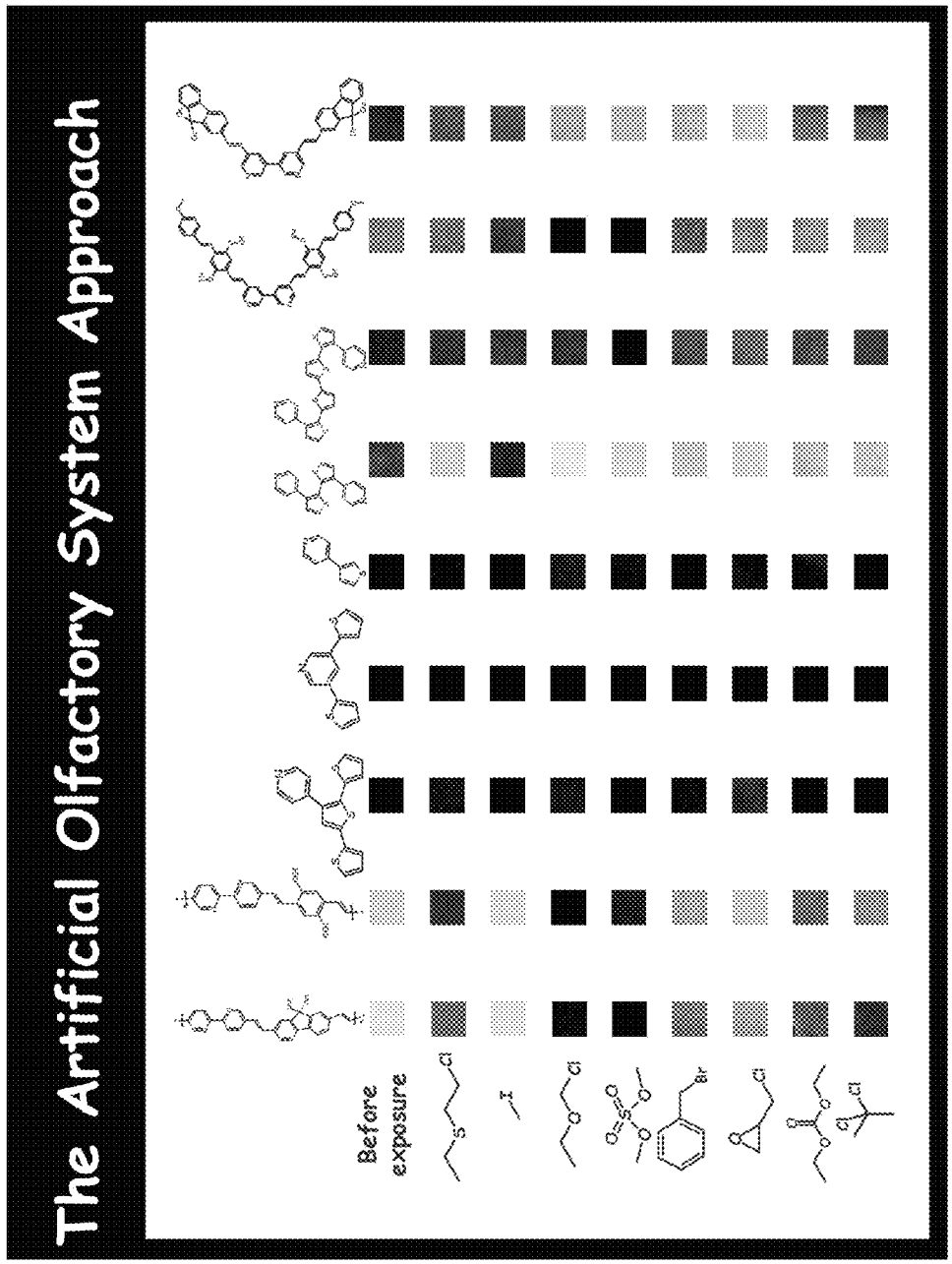

FIG. 4 shows the identification of seven alkylating agents (in left most column) using an array of nine chemosensors (in top row). Emission was measured after being excited with a 365 nm light source.

Figure 5:
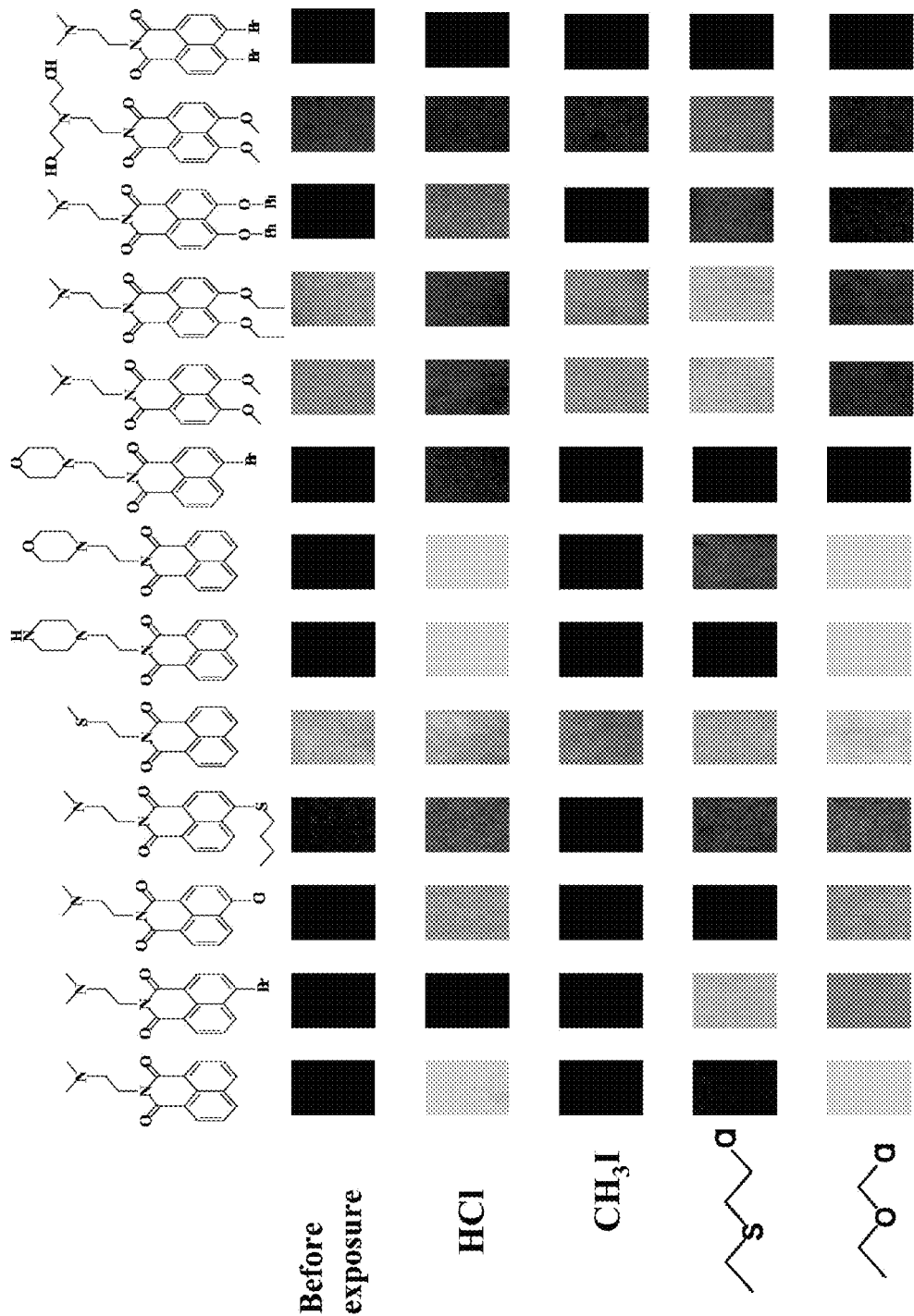

FIG. 5 shows the identification of four alkylating agents (in left most column) using an array of thirteen chemosensors (in top row). Emission was measured after being excited with a 365 nm light source.

Figure 6:
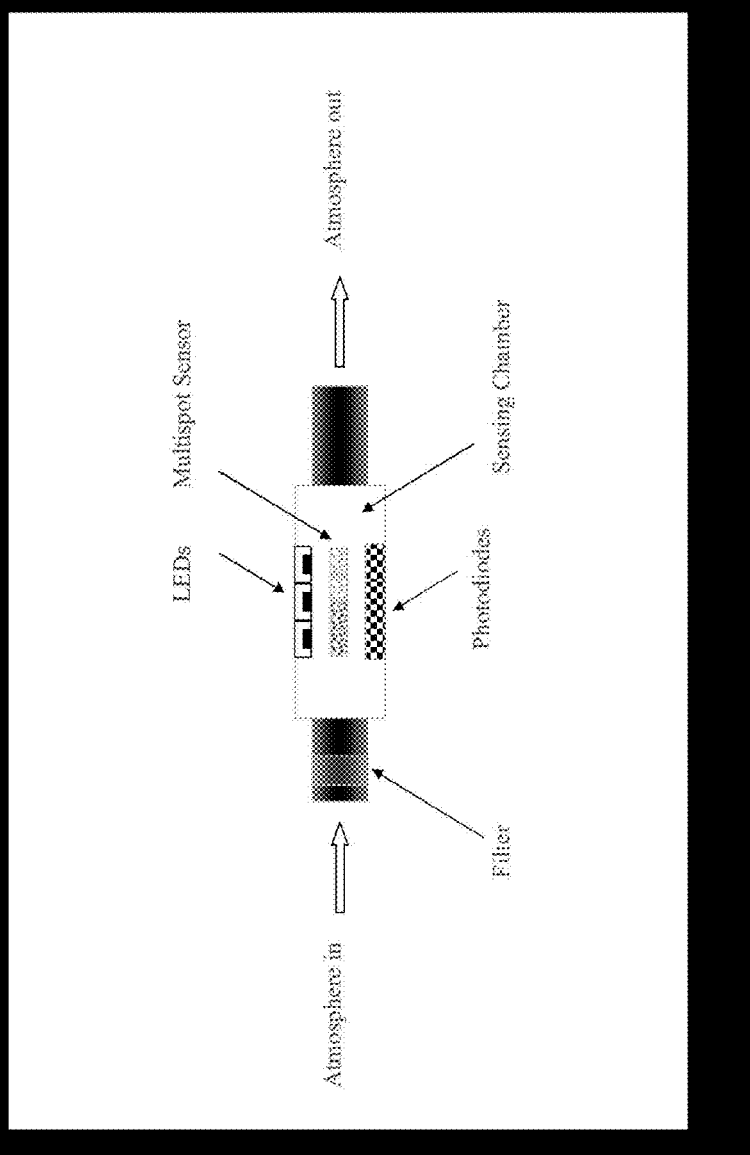

FIG. 6 shows a device for identifying a molecule containing an electrophilic or nucleophilic moiety from an atmospheric sample.

DETAILED DESCRIPTION OF THE INVENTION

The present invention provides methods for identifying a molecule in a sample, the molecule includes an electrophilic or nucleophilic moiety. In one method, the sample is contacted with a plurality of chemosensors, each of the chemosensors having a π-conjugated system and a moiety having a nucleophilic property or an electrophilic property. An electromagnetic property of each of said chemosensors in the sample is then measured. The pattern of changes in the electromagnetic properties of the plurality of chemosensors after chemically reacting with said electrophile or nucleophile of said molecule can identify the molecule in the sample.

The molecule can be identified when it is one of two unknowns in a sample, or one of three, four five, ten, twelve, fifteen, twenty, twenty five, thirty, fifty, one hundred or more unknown molecules in the sample.

The present invention also provides a device for the identification of a molecule that is an electrophile or nucleophile. The device includes a substrate carrying a plurality of chemosensor molecules having at least one predetermined electromagnetic property. This electromagnetic property can change by introducing the chemosensor molecules to a sample containing the molecule that is an electrophile or nucleophile. The pattern of change of the electromagnetic property of the plurality of chemosensor molecules allows the device to identify said electrophile or nucleophile in the sample.

The term "chemosensor" refers to a molecule having a π-conjugated system and a reacting (nucleophilic or electrophilic) moiety capable of reacting with at least one electrophilic or nucleophilic molecule, respectively.

In one embodiment, the chemosensor has the formula A-B, where A includes a π-conjugated system, and B includes a nucleophilic or electrophilic moiety. Optionally, A and B are π-conjugated to each other. In another embodiment, the chemosensor has the π-conjugated property and the nucleophilic or electrophilic property in one moiety. The chemosensor employed is typically one which is capable of absorbing and/or emitting electromagnetic radiation.

As a person skilled in the art would recognize, the use of a singular form of the term "chemosensor" is not to be interpreted literally but rather should be taken to mean a plurality of such chemosensor molecules having the measurable electromagnetic characteristics. The plurality of chemosensors can each be in a separate place or in a mixture in the same place.

In one embodiment of the invention, the method is based on photo-induced electron transfer quenching of a chemosensor of the general structure A-B, wherein A is a luminophore being quenched by the nucleophile (or Lewis base) moiety B. The luminophore is typically a chemosensor, or part thereof, that both absorbs and emits light. As such, within the scope of the invention, luminophores include chromophores, fluorophores, phosphors, chemiluminophores and all other molecular, supramolecular and macromolecular species that emit light. Herein, the term luminophore also includes any intercalator-type moiety complexing agent or any other agent necessary to alter the conformation of the luminophore, or otherwise affect its luminescence, when the chemosensor or the device associated therewith interacts with the electrophile.

In one embodiment, moiety B is an integral part of A; such is the case with heteroaromatic moieties (e.g., quinolyl, pyridyls, thiophenyls) having a π-conjugated backbone and a nucleophilic heteroatom.

In yet another embodiment, A is an aromatic or heteroaromatic moiety or a π-conjugated system having a pendant nucleophile or electrophile B. The aromatic or heteroaromatic moiety or π-conjugated system may be selected, in a non-limiting fashion, from naphthalene, anthracene, quinoline, isoquinoline, pyridine, thiophene, furan, quinolizine, imidazole, pyrimidine, tetrazole, pyrrole, thiazole, isothiazole, oxazole, isoxazole, triazole, and derivatives thereof and others as may be known to a person skilled in the art.

When B is a nucleophilic moiety (or the quencher of a photo-induced electron transfer process) it is a group or an atom capable of interacting with the electrophile. Such group or atom may be a neutral or charged Lewis base. Non-limiting examples of such Lewis base group are —OH, —OR, —SH, —SR, —NH$_2$, —NHR, —NRR' and —N=R—, in their neutral or charged forms (i.e., the charged form of —OH is its hydroxide). The Lewis base group or atom may be tethered to the π-conjugated moiety (e.g., luminophore) directly, namely via a single, double or triple bond, or via a linker moiety which may or may not be conjugated to the π-conjugated moiety.

When B is an electrophilic moiety, (or the quencher of a luminescence process of A) it is a group or an atom capable of interacting with the nucleophile. Such group or atom may be a neutral or charged Lewis acid or a leaving group which is a part of the molecule that detaches from it upon reaction with the nucleophile. Non-limiting examples of such Lewis acids and leaving groups include hydrogen, acid halides, esters, thio esters, sulfonic esters, amides and ethers. The Lewis acid or leaving group or atom may be tethered to the π-conjugated moiety (e.g., luminophore) directly, namely via a single, double or triple bond, or via a linker moiety which may or may not be conjugated to the π-conjugated moiety.

In one embodiment the leaving group is a group bearing one or more iodine atoms. In the bound state, the luminescence of the luminophore is quenched, among other processes, through spin-orbit coupling. Upon reaction with the nucleophile, the group containing the iodine atoms is released from the luminophore, thus regaining its luminescence.

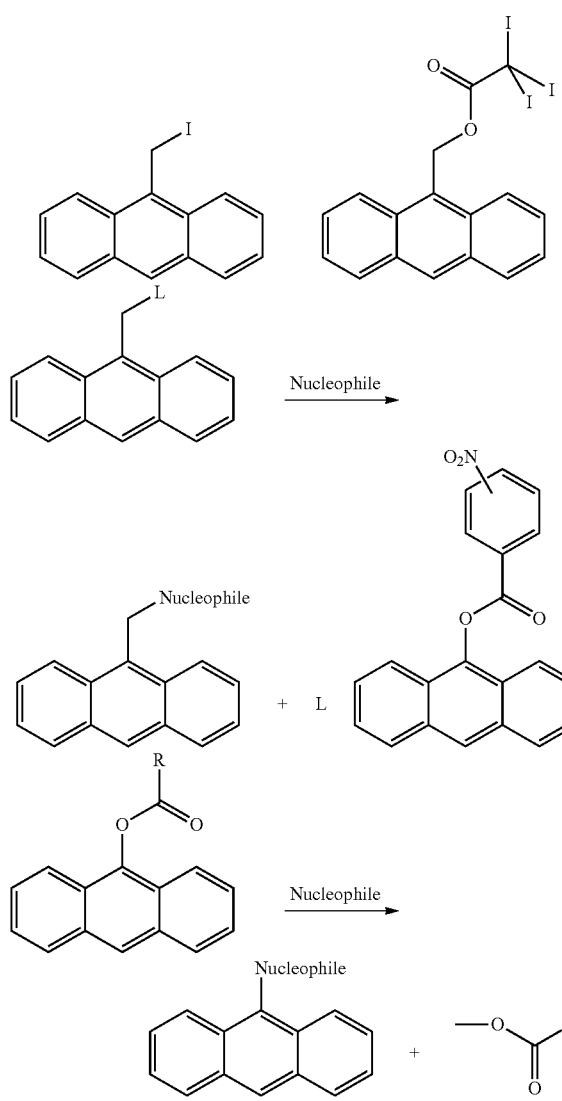

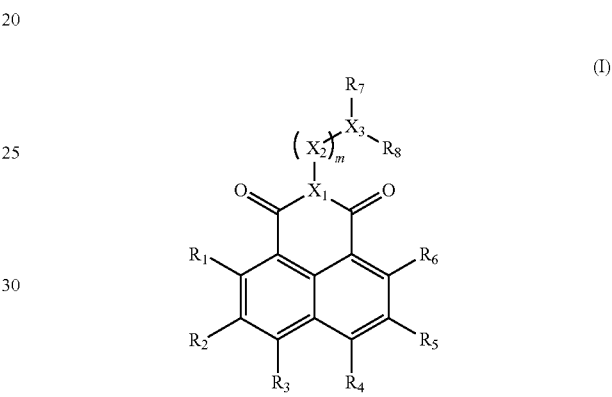

In another embodiment, the electromagnetic property measured is the change in the electron density of the highest occupied molecular orbital (HOMO) or lowest unoccupied molecular orbital (LUMO) or the change in the location of the HOMO or LUMO. Such change can be measured, for example, by absorption, luminescence or refractive index.

The term "π-conjugated" or any lingual variation thereof, refers to a molecular entity having a system of alternating single and multiple bonds: e.g., —CH=CH—CH=CH—, —CH=CH—C=N—, —CH=CH—C≡CH, —CH=CH=C—. In such systems, conjugation is the interaction of one P-orbital with another across an intervening σ-bond. The term is also extended to the analogous interaction involving a P-orbital containing an unshared electron pair, e.g., Cl—CH=CH$_2$.

In one embodiment, the chemosensors are those where the π-conjugation is aromatic or heteroaromatic. In another embodiment, the chemosensors are those where the π-conjugated moiety is acyclic, or cyclic but non-aromatic.

π-conjugated chemosensors may include unsaturated alkyl groups having at least two carbon atoms with one or more sites of unsaturation, the groups being known as alkenyl groups or radicals and alkynyl groups or radicals, as defined hereinbelow. The sites of unsaturation may be one or more double or triple bonds, or a mixture thereof, structured linearly or may in a branched configuration.

Non-limiting examples of mixed n-conjugated moieties are 2-methyl-1-buten-3-yne, 2-methyl-1-hexen-3-yne and the like. Mixed alkenyl and alkynyl groups may be unsubstituted or substituted.

In another embodiment of the structure A-B, either A or B or each is bonded to at least one amino acid residue. The bonding between the amino acid residue and the chemosensor (through moiety A, or B, or each) is via the C-terminal (e.g., as an ester), N-terminal (e.g., as an amine) or the α-carbon atom of the amino acid. In the case of α-substituted amino acid residues such as lysine, the bonding with the chemosensor moiety may be via any atom of the α-substituent.

In another embodiment of the general structure A-B, the chemosensor is of the general formula (I):

(I)

wherein $R_1$ to $R_6$ may each, independently of each other, be selected from H, $C_1$-$C_{10}$ alkyl, $C_1$-$C_{10}$ alkylene, $C_2$-$C_{10}$ alkenyl, $C_2$-$C_{10}$ alkenylene, $C_2$-$C_{10}$ alkynyl, $C_2$-$C_{10}$ alkynylene, $C_1$-$C_{10}$-alkylamine, alkoxy, cycloalkyl, cycloalkylene, $C_6$-$C_{19}$ aryl, $C_6$-$C_{10}$ arylene, $C_5$-$C_{15}$ heteroaryl, —O(O=C)—, —(C=O)O—, —NO$_2$, —NR'R", —OH, halide, amino acid residue and derivatives thereof, peptide and derivatives thereof, fatty acid residue and derivatives thereof, and sugar residue and derivative thereof;

wherein each of said R' and R", independently of each other is selected amongst H, $C_1$-$C_{10}$ alkyl, $C_1$-$C_{10}$ alkylene, $C_6$-$C_{10}$ aryl, $C_6$-$C_{10}$ arylene, aralkyl, $C_5$-$C_{15}$ heteroaryl, heteroarylene;

R' and R" together with the N atom to which they are bonded may form a 5- or 6-membered carbocyclic or heterocyclic ring system containing optionally at least one additional heteroatom selected from N, O and S;

each proximate $R_1$ to $R_6$ ($R_1$ and $R_2$, $R_2$ and $R_3$, $R_3$ and $R_4$, $R_4$ and $R_5$, and/or $R_5$ and $R_6$) together with the carbon atoms to which they are bonded may form a 5- or 6-membered ring containing optionally at least one heteroatom selected from N, O and S;

$X_1$ is an atom selected from C and N; when $X_1$ is C, it may be connected to $X_2$ via a single, double or triple bond;

$X_2$ is a carbon group selected from $C_1$-$C_{10}$ alkylene, $C_2$-$C_{10}$ alkenylene, $C_2$-$C_{10}$ alkynylene, $C_1$-$C_{10}$ ethers or polyethers, cycloalkylene, and $C_6$-$C_{10}$ arylene;

m is an integer between 1 and 10;

$X_3$ is an atom having at least one lone pair of electrons, being preferably selected from N, O or S either in their neutral form or negatively charged, and more preferably selected from —$NR_7R_8$, —$OR_7$, or —$SR_7$; and $R_7$ and $R_8$, independently of each other may be H or $C_1$-$C_5$ alkyl.

In one embodiment of the general formula I, at least one of $R_1$ to $R_6$ is not H.

In another embodiment of the general formula I, either $R_3$ or $R_4$ or both are not H.

In another embodiment of the general formula I, each of $R_1$, $R_2$, $R_5$ and $R_6$ is H and $X_2$ is —$CH_2$— and m is an integer between 1 and 5.

In another embodiment of the general formula I, $R_3$ and $R_4$ are each a $C_1$-$C_{10}$-alkoxy, $X_2$ is —$CH_2$—, m is an integer between 1 and 5 and $X_3$ is —$NR_7R_8$, wherein each of $R_7$ and $R_8$, independently of each other is a $C_1$-$C_5$ alkyl group.

In another embodiment of the general formula I, each of $R_7$ and $R_8$, independently of each other is a methyl, ethyl, propyl or iso-propyl group.

In another embodiment of the general formula I, each of $R_3$ and $R_4$, independently of each other is a $C_1$-$C_5$ alkoxy.

In another embodiment, the chemosensor of the general formula I is N-(2-dimethylaminoethyl)-1,8-naphthalimide or a ring-substituted derivative thereof of the general formula II:

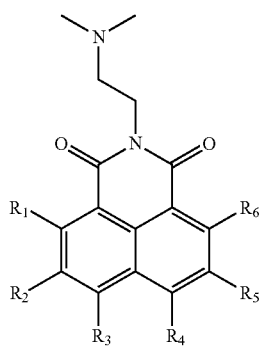

(II)

wherein each of $R_1$ to $R_7$ is as defined above.

In another embodiment, the chemosensor of the general formula I is N-(2-dimethylaminoethyl)-1,8-naphthalimide, herein designated Compound 1:

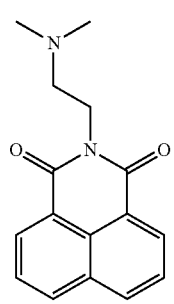

Compound 1

In another embodiment, the chemosensor of the general formula II is a ring-substituted $C_1$-$C_{10}$ alkoxy derivative of Compound 1, wherein in the general formula II each of $R_1$ to $R_6$ is independently selected from $C_1$-$C_{10}$ alkoxy.

In another embodiment, in the derivative of Compound 1 at least one of $R_1$ to $R_6$ is not H. In another embodiment, either R3, or R4 or both are not H.

In still another embodiment, the chemosensor of the general formula II is N-(2-dimethylaminoethyl)-4,6-diethoxy-1,8-naphthalimide, herein designated Compound 2:

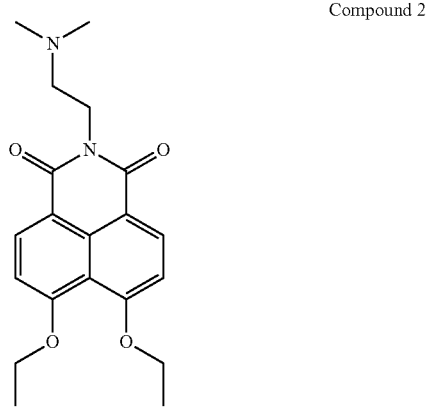

Compound 2

In another embodiment, the chemosensor of the general formula II is N-(2-dimethylaminoethyl)-4,6-dimethoxy-1,8-naphthalimide, herein designated Compound 3:

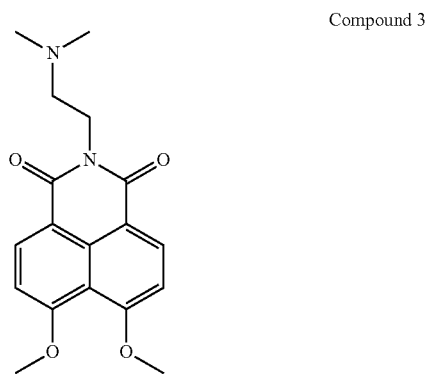

Compound 3

In another embodiment, the chemosensor of the general formula II is a ring-substituted amino-acid derivative of Compound 1, wherein each of $R_1$ to $R_6$ is independently selected amongst an amino-acid residue. The amino-acid substitution may be via the α-carbon of the amino acid residue or through the C or N terminal thereof. The amino acid residue may be selected from substituted or unsubstituted isoleucine, leucine, asparagines, alanine, phenylalanine, lysine, methionine, cysteine, glutamate, threonine, glutamine, tryptophan, glycine, valine, praline, arginine, serine, histidine, and tyrosine. In another embodiment, the amino acid residue is substituted or unsubstituted lysine.

In another embodiment, the chemosensor of the general formula I is N-(2-dimethylaminoethyl)-4-(N'-(N-Boc-lysinyl)-1,8-naphthalimide, herein designated Compound 4:

Compound 4

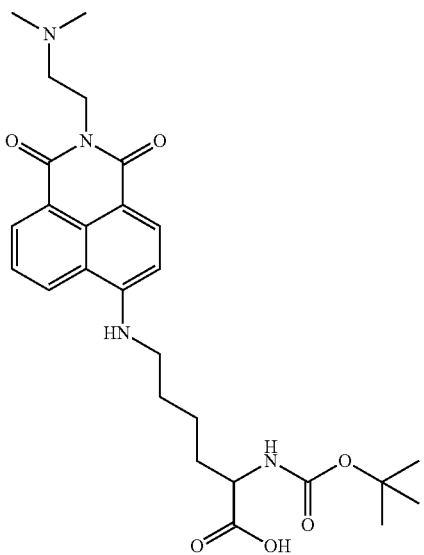

The term "alkyl" refers within the context of the present invention to a straight, branched or cyclic, in certain embodiments straight or branched, divalent aliphatic hydrocarbon group, having from 1 to 10 carbon atoms. When the alkyl group is substituted on both of its ends, it is referred to herein as an alkylene.

There may be optionally inserted along the alkyl or alkylene group one or more oxygen, sulfur, including —S(═O)— and —S(═O)$_2$— groups, or substituted or unsubstituted nitrogen atoms including —NR— and —N$^+$RR— groups, where the nitrogen substituent(s) is(are) alkyl, aryl, aralkyl, heteroaryl, heteroaralkyl or —COR', where R' is alkyl, aryl, aralkyl, heteroaryl, heteroaralkyl, —OY or —NYY, where Y is hydrogen, alkyl, aryl, heteroaryl, cycloalkyl or heterocyclyl. Alkyl groups include, but are not limited to, methyl, ethyl, propyl, butyl, isopentyl, hexyl, dodecyl and others as may be known to a person skilled in the art.

The alkyl group may be optionally substituted by at least one group selected from halogens, pseudohalogens, alkoxides, phenols, alkyls, alkenyls, alkynyls, —NO$_2$, —CN, —SCN, —OCN and others, or any combinations therewith.

The alkyl of the alkyl halide may be an inner-chain alkylene group, with the halide atom being connected to the alkylene segment. Alkylene groups may for example be methylene (—CH$_2$), ethylene (—CH$_2$CH$_2$—), propylene (—(CH$_2$)$_3$—), methylenedioxy (—O—CH$_2$—O—) and ethylenedioxy (—O—(CH$_2$)$_2$—O—).

The term "cycloalkyl" refers within the context of the present invention to a divalent saturated mono- or multicyclic ring system, having between 3 and 10 carbon atoms, more preferably between 3 and 6 carbon atoms. The ring systems of the cycloalkyl may be composed of one ring or two or more rings which may be joined together in a fused, bridged or spiro-connected fashion. When the cycloalkyl is substituted on both ends, it is referred to herein as a cycloalkylene group.

As used herein, "alkenyl" refers to a straight, branched or cyclic divalent aliphatic hydrocarbon group, having from 2 to 10 carbon atoms and at least one double bond. There may be optionally inserted along the alkenyl group one or more O, N or S or substituted or unsubstituted nitrogen atoms, where the nitrogen substituent is preferably alkyl. Alkenylene groups are mid-chain alkenyls, non-limiting examples of which are —CH═CH—CH═CH— and —CH═CH—CH$_2$.

The term "alkynyl" refers to a straight, branched or cyclic divalent aliphatic hydrocarbon group, having from 2 to 10 carbon atoms and at least one triple bond. There may be optionally inserted along the alkynyl group one or more O, N or S or substituted or unsubstituted nitrogen atoms, where the nitrogen substituent is preferably alkyl. Alkynylene groups are mid-chain alkynyls. Non-limiting examples of alkynyls include —C≡C—C≡C—, —C≡C— and —CδC—CH$_2$—.

The term "halide" or "halo" refers to an atom selected from F, Cl, Br and I.

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl. The term "arylene" refers to a monocyclic or polycyclic aromatic group, having from 6 to 10 carbon atoms and at least one aromatic ring. Arylene groups include, but are not limited to, 1,2-, 1,3- and 1,4-phenylene.

The term "heteroaryl" refers to a monocyclic or multicyclic aromatic ring system containing between 5 15 atoms, where one or more thereof being an heteroatom, namely an atom being different from C. Preferably, the heteroatom is selected from N, O and S. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl and isoquinolinyl. The term "heteroarylene" refers to a divalent monocyclic or multicyclic aromatic ring system, having between 6 and 10 atoms in the ring(s), where one or more of the atoms in the ring system is different from C, and being preferably selected from N, O or S.

The term "aralkyl" refers to an alkyl group, as defined above, in which one of the hydrogen atoms of the alkyl is replaced by an aryl group, as defined.

The term "alkoxy" refers to RO— in which R is alkyl, as defined above. Non-limiting examples are methoxy, ethoxy, propoxy, pentoxy, etc. The term also encompasses R groups which are aryls or heteroaryls as defined.

The term "alkyl amine" refers to an alkyl group, as defined above, substituted by at least one amine group. The amine group is generally of the structure —NRR, wherein each R group may be, independently of each other, selected from H, alkyl, aryl, heteroaryl, cycloalkyl or heterocyclyl, as defined above. The amine group may also be a quaternary amine having a positive charge. In such a case, the ammonium group is accompanied by at least one counter-ion selected from organic and inorganic anions, as may be known by a person skilled in the art.

The term "derivative" refers to a substituted or a main fragment of the parent compound, as may be known to a person skilled in the art. Preferably, the derivative of a certain chemosensor molecule is one which maintains the general structure of the parent compound (e.g., chemosensor as defined above) and its electromagnetic properties.

The term "substituent" or any lingual variation thereof is an art-recognized term which refers to the replacement of an atom or a functional group with another atom or functional group. The substitution of the parent chemosensor molecule disclosed herein may be of one or more alkyl, alkenyl, alkynyl, cycloalkyl, cycloalkenyl, cycloalkynyl, aryl, heteroaryl, heterocyclyl, alkylene, alkenylene, alkynylene, cycloalkylene, cycloalkenylene, cycloalkenylene, arylene, heteroarylene and heterocyclylene groups, as defined herein. Within the scope of this definition, a "ring-substituted derivative" refers specifically to a substitution on the ring system of the chemosensor molecule or on the ring system of a pendant substituent. A person skilled in the art would recognize, for example that in the chemosensor of the general formula I the ring system is the naphthalene system.

In other embodiments, the chemosensor is an oligomer or polymer associated with a plurality of pendant chemosensor moieties each having at least one π-conjugated group and at least one nucleophilic group. The association of the oligomer or polymer with each of said chemosensor moieties is preferably irreversible and may be via any type of chemical bonding or physical interaction known, e.g., covalent bonding, electrostatic interaction, hydrogen bonding, etc. Preferably, such interaction or association does not impose any constrains on or limit the activity of the chemosensor moieties.

In some preferred embodiments, the association is via π-conjugation. The type of association with each of the chemosensor moieties, however, may change as a result of the interaction between the chemosensor moieties and the electrophiles or nucleophiles, respectively.

In yet another embodiment, the chemosensor is the backbone of the oligomer or polymer, at least one part thereof acting as a π-conjugated moiety (A), at least another part thereof acting as a nucleophilic moiety (B) with the two parts being connected to each other via π-conjugation.

In still other embodiments, the oligomer or polymer may be constructed of repeating π-conjugated groups (A), each being in conjugation with the other, while the nucleophilic groups (B) are pendant side group which are also in conjugation with the backbone itself.

The term "oligomer or polymer" refers to a molecular structure having a backbone which may be fully linear or optionally having pendant moieties. The backbone is typically constructed of the same or different repeating units, connected either directly via a single, double or triple bond, or indirectly via a mid-group such as an alkylene, alkenylene, alkynylene, arylene etc.

The oligomers contain between 1 and 10 repeating units. The polymers contain at least 11 repeating units.

Non-limiting examples of such oligomers and polymers useful in the invention are oligo(poly)styrenes, oligo(poly)acetylenes, oligo(poly)ethylene oxides, oligo(poly)ethylenes, oligo(poly)pyridines, oligo(poly)siloxanes, oligo(poly) phenylenes, oligo(poly)thiophenes, oligo(poly) pyrroles, oligo(poly) (phenylenevinylene)s, oligo(poly) silanes, oligo(poly)ethylene terephthalates, oligo (poly) (phenylene ethynylene)s and other oligo(poly)arylenes and heteroarylenes, oligo(poly)arylene vinylenes, oligo(poly) arylene ethynylenes, and derivatives thereof.

Specific repeating units for such oligomers/polymers are:
(1) oligo(poly) arylenes and heteroarylenes having the following monomers:

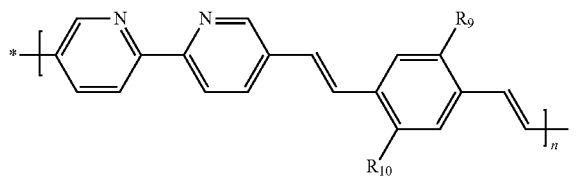

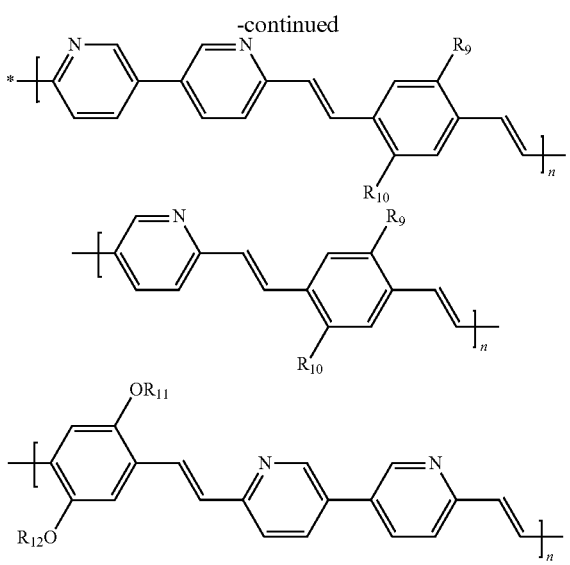

(2) oligo(poly) thiophenes having the following monomers:

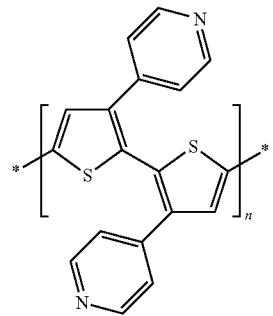

And hetero oligo/polymers of the types like

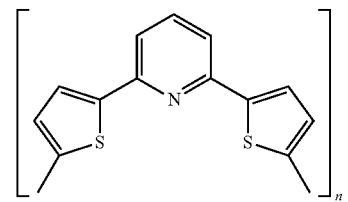

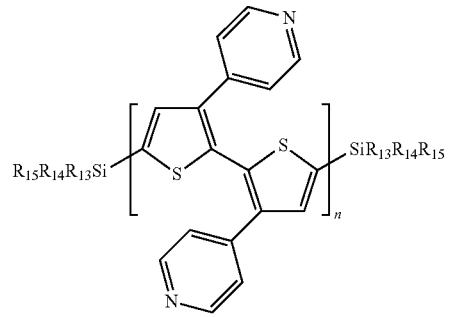

wherein each of groups $R_9$ and $R_{10}$, independently of each other, may be selected from H, $C_1$-$C_{10}$ alkyl, $C_1$-$C_{10}$ alkylene, $C_2$-$C_{10}$ alkenyl, $C_2$-$C_{10}$ alkenylene, $C_2$-$C_{10}$ alkynyl, $C_2$-$C_{10}$ alkynylene, $C_1$-$C_{10}$-alkylamine, $C_1$-$C_{10}$ alkoxide, cycloalkyl, cycloalkylene, $C_6$-$C_{10}$ aryl, $C_6$-$C_{10}$ arylene, —O(O=C)—, —(C=O)O—, —$NO_2$, —NR'R", —OH, halide, and —$(X_2)_n$—$(X_3)R_7R_8$;

each of groups $R_{11}$ and $R_{12}$, independently of each other, may be selected from H, $C_1$-$C_{10}$ alkyl, $C_1$-$C_{10}$ alkylene, $C_2$-$C_{10}$ alkenyl, $C_2$-$C_{10}$ alkenylene, $C_2$-$C_{10}$ alkynyl, $C_2$-$C_{10}$ alkynylene, $C_1$-$C_{10}$-alkylamine, $C_1$-$C_{10}$ alkoxide, cycloalkyl, cycloalkylene, $C_6$-$C_{10}$ aryl, $C_6$-$C_{10}$ arylene, and —$(X_2)_n$—$(X_3)R_7R_8$;

each of groups $R_{13}$ to $R_{15}$, independently of each other, may be selected from H, $C_1$-$C_{10}$ alkyl, $C_1$-$C_{10}$ alkylene, $C_2$-$C_{10}$ alkenyl, $C_2$-$C_{10}$ alkenylene, $C_2$-$C_{10}$ alkynyl, $C_2$-$C_{10}$ alkynylene, $C_1$-$C_{10}$-alkylamine, alkoxide, cycloalkyl, cycloalkylene, $C_6$-$C_{10}$ aryl, $C_6$-$C_{10}$ arylene, —NR'R", —OH, —O(O=C)—, —(C=O)O—, and —$(X_2)_n$—$(X_3)R_7R_8$;

wherein each of said R' and R", independently of each other is selected amongst alkyl, aryl, aralkyl, heteroaryl, heteroaralkyl;

R' and R" together with the N atom to which they are bonded may form a 5- or 6-membered carbocyclic or heterocyclic ring system containing optionally at least one additional heteroatom selected from N, O and S;

n is an integer being equal or greater than 1; for an oligomer n is an integer between 1 and 10 and for a polymer n is greater than 11, most preferably not greater than 100;

and wherein $X_2$, $X_3$, $R_7$, $R_8$ and n are as defined hereinabove with respect to general formula I.

In the above exemplified oligomeric and polymeric chemosensors, the π-conjugated moiety (A) may be the π-conjugated backbone of the oligomer or polymer. The nucleophilic moiety (B) may be the heteroatom of the thiophene or pyridine rings or any pendant group bonded to the conjugated backbone. The pendant groups may be substituted as shown in case of groups $R_9$ and $R_{10}$ or by any other sequence along the conjugated chain.

As discussed above, the present invention provides methods for identifying a molecule in a sample, the molecule includes an electrophilic or nucleophilic moiety. In one method, the sample is contacted with a plurality of chemosensors, each of the chemosensors having a π-conjugated system and a moiety having a nucleophilic property or an electrophilic property. An electromagnetic property of each of said chemosensors in the sample is then measured. The pattern of changes in the electromagnetic properties of the plurality of chemosensors after chemically reacting with said electrophile or nucleophile of said molecule can identify the molecule in the sample.

In one aspect, the chemosensor, when containing a nucleophilic moiety, chemically reacts, for example by covalent bonding, with an electrophilic molecule in the sample. In another aspect, the chemosensor, when containing an electrophilic moiety, chemically reacts with a nucleophilic molecule in the sample.

The electromagnetic property can be, for example, optical, conduction, induction, permeability, potential or dielectric properties. Optical properties include, for example, intensity, quantum yield, polarization, lifetime, excitation, emission wavelength and refractive index.

The molecule in the sample can be inorganic or organic. The molecule can be an electrophile, for example, an alkylating agent.

The sample can be from the atmosphere, for example. The sample can be biological in origin. The sample can contains two or more different molecules.

The chemosensors can be in solution or immobilized on a solid or semi-solid support. The solid support can be, for example, a bead or particle, a microsphere, a nanobead, glass, a flexible membrane, a semi-rigid or rigid membrane, a plastic, a metal or a mineral surface. The chemosensors can be in a gel or a matrix. A plurality of chemosensors can be used, for example, 2, 5, 10, 20, 30, 40, 50, 60, 70, 80, 90, 100 or more.

In another aspect of the invention, there is provided a system for identifying at least one electrophile in a sample for carrying out the method of the invention.

In one embodiment, the system comprises a media associated with the chemosensors allowing the formation of an electrophile-bound (or nucleophile-bound) chemosensor and the detection thereof. This media may for example be the solution in which the at least one chemosensor is dissolved, the gel or matrix in which it is impregnated or the solid or semi-solid substrate on which it is deposited.

In yet another embodiment there is provided a composition including:

(i) media adapted to support interaction between at least one electrophile or nucleophile and chemosensors having at least one measurable electromagnetic property;

(ii) a plurality of chemosensors where in response to binding to at least one electrophile or nucleophile the chemosensor molecules each undergo a change in said at least one electromagnetic property; and (iii) a detector adapted to detect the change in said at least one electromagnetic property. The pattern of change can identify the electrophile or nucleophile.

Chemosensors may be in solution, impregnated in a gel or a matrix, loaded on a solid or semi solid support, attached to a fiber optic probe, etc.

In another embodiment, there is provided a composition including:

(i) chemosensors immobilized on a solid or semi-solid support (as defined hereinabove);

(ii) a means for allowing the interaction between the chemosensors and an electrophile or nucleophile; and (iii) a means for detecting (as defined hereinabove) the interaction and the formation of an electrophile-bound (or nucleophile-bound) chemosensor.

According to another aspect of the invention, there is provided a device for the detection of an electrophile or nucleophile. The device includes a substrate carrying a plurality of chemosensor molecules having at least one predetermined electromagnetic property. The electromagnetic property can be changed by subjecting the chemosensor molecules to a media (e.g., sample) containing at least one electrophile or nucleophile.

According to yet another aspect of the invention there is provided a sensor device configured and operable for sensing an electrophile or nucleophile. The device includes a plurality of chemosensor molecules selected to be capable of changing an electromagnetic property in response to a reaction with the electrophile or nucleophile. The pattern of change in the plurality of chemosensor molecules is read by the device and identifies the electrophile or nucleophile.

It should be understood that, whenever possible, descriptions or examples of a nucleophilic chemosensor reacting to an electrophile also apply to an electrophilic chemosensor reacting with a nucleophile.

The chemosensor is said of having a "measurable electromagnetic property", namely an electromagnetic property of the chemosensor that is capable of being perceived, either by direct observation or instrumentally, and the presence or magnitude of which is a function of the presence of an electrophile in the sample. This change in an electromagnetic property may include optical, conduction, induction, permeability, potential, and dielectric properties. The optical property may be a change in intensity, quantum yield, polarization, lifetime, a shift in excitation or emission wavelength or a combination of these effects. Spectral changes that result in an enhancement or quenching of the intensity or a shift in the wavelength of the emission or excitation are preferred.

The electromagnetic property of the chemosensor prior to association with the electrophile or nucleophile may be a known property or may be measured. Preferably, for example, in order to allow detection of the electrophile via the formation of the electrophile-bound chemosensor, the measurable electromagnetic property of the chemosensor should be different from the electromagnetic property of the electrophile-bound chemosensor.

Once the nucleophilic moiety of the chemosensor undergoes binding (or association) with the electrophile, a new electromagnetic signal, now associated with the newly formed electrophile-bound chemosensor, is observed, thus affording a measurable qualitative and quantitative interaction. The binding that results from contact between the electrophile and the chemosensor results in the formation of an electrophile-bound chemosensor. The binding between the two may be any chemical or physical interaction which is associated with a change in the at least one electromagnetic property of the chemosensor (e.g., optical property). The binding type (or chemical reactivity) may be selected from covalent, ionic, hydrogen bonding, electrostatic, ligation, complexation, and others as may be known to skilled person in the art.

The binding between the chemosensor and the electrophile may result in the formation of a charged nucleophile, such as in the case of quaternary ammonium compounds. Alternatively, the chemosensor may be neutral. In some embodiments, the binding may be equimolar, namely a 1:1 ratio of electrophile to nucleophile or in different ratios, such as 1:2 nucleophile:electrophile, respectively.

In some other embodiments, the binding is reversible, allowing re-usable sensor device.

The detection of the change in the at least one electromagnetic property after interaction is preferably measured identically and by the same methods employed to measure the radiation of the free chemosensor.

In some embodiments, however, the chemosensor may not have a detectable and thus measurable radiation until it interacts with the electrophile to form the electrophile-bound chemosensor.

Examples of optical signals include changes in the optical properties, including, but not limited to, a change in color, changes in intensity (absorbance or fluorescence) at the same or different wavelengths, a spectral (absorption or emission) shift, changes in lifetime of luminescence (fluorescence, phosphorescence, and the like) and changes in refractive index.

Changes in the electromagnetic properties, preferably optical properties, of the chemosensor upon binding the electrophile are detected qualitatively, or optionally quantitatively, by detection of the resultant light emission. The amount of signal generated by the binding of the chemosensor to the electrophile can be correlated to the concentration by methods that will be known to the skilled artisan. For example, the artisan may determine the concentration of the electrophile in a sample by comparing the signal generated with a reference measurement, wherein the reference measurement is the amount of signal generated when the chemosensor is bound to a known quantity of the electrophile.

Various techniques are known to those in the art for measuring the time dependence of e.g., fluorescence emission, including streak cameras, time correlated single photon counting, direct measurement of the time resolved fluorescence, upconversion techniques, phase-sensitive detection, boxcar techniques, and the like. Similarly, while lasers as light sources and photomultiplier tubes as detectors have been used, for some applications adequate or improved performance may be achieved by the use of LED's, laser diodes, electroluminescent sources, arc lamps, spark gaps, xenon arc lamps, incandescent lamps, or other sources. In the same fashion other light detectors may be used, including microchannel plate photomultiplier tubes, photodiodes, avalanche photodiodes, streak cameras, CCD's and other detectors known to the art may be used.

The π-conjugated moiety of the chemosensor has delocalized π-electrons capable of emitting luminescence including UV and visible radiation, e.g., as measured with respect to the energy used to excite the chemosensor. The π-conjugated moiety may be linear, branched, or cyclic, and may or may not comprise mid-chain heteroatoms such as N, O or S. The π-conjugated moiety may or may not be composed of the same units (homopolymer, copolymer).

The term "electrophile" refers in the context of the present invention to a compound having reactivity towards species with available electron density, i.e. a Lewis acid and a nucleophile. The electrophile is preferably an organic Lewis acid. More preferably, the electrophile is an organic alkylating agent.

In one preferred embodiment, the organic electrophile is an alkyl halide (or alkylene halide, cycloalkyl halide, cycloalkylene halide and other halide substituted carbon based systems), having between 1 and 20 carbon atoms.

In some preferred embodiments, the electrophile is further substituted or has at least one mid-chain heteroatom selected from N, O, S, or P. Such atoms may be oxidized or non-oxidized.

The electrophile may be selected, without being limited thereto, from halobenzyl, mono- or dihalomethane, mono- or dihalodiethyl sulfide, mono- or dihalo diethylether, mono- or dihalo ethylmethyl sulfide, mono- or dihalo ethylmethylether, and any substituted derivatives thereof.

Non limiting examples of electrophiles that may be detected according to the invention may include blister agents such as nitrogen or sulfur mustards, nerve agents, e.g., sarin, phosgene, soman, tabun and thionyl chloride, herbicides, pesticides or insecticides, e.g. 1,2,3,4,10-hexachloro-1,4,4a,5,8,8a-hexahydro-1,4,5,8-dimethano naphthalene, 1,2,3,4,5,6-hexa-chlorocyclohexane, 4,4'-(2,2,2-trichloroethane-1,1-diyl)bis(chlorobenzene), dichloro-diphenyldichloroethylene, 1,1-dichloroethane, 1,2-dichloroethane, toxaphen, heptachlor, endosulfan, and others known in the art.

The term "sample" or "media" refers to a medium in which the organic electrophile may be contained. Such a sample may be solid, liquid, gaseous, any mixture of either combination or a solution; it may comprise one or more other organic and/or inorganic compounds and/or any one biological agent; it may be pure or contaminated; it may contain a mixture of known and unknown components; and it may require prior processing.

The sample may be a test sample of known concentration, or a test sample used to calibrate the detection of the electrophile or may be an environmental sample such as soil, water, atmospheric medium, rain, snow, etc., suspected of containing at least one electrophile.

The sample may be an aqueous solution or may be a solution collected directly from the environment such as a stream, ditch or water supply. Alternatively the solution could be prepared by dissolving a solid sample which is believed of being contaminated with at least one electrophile in an appropriate solvent. In such a case, the solid sample is tested after dissolution in accordance with the present method.

In some cases, the detection of the electrophile may necessitate the use of at least one additional agent such as an acid or a base or at least one additional solvent which is different from the solvent constituting the media of the sample. In such cases, the sample may be treated by adding thereto an amount of said agent, prior to contacting thereof with the chemosensor or thereafter.

The term "photo-induced electron and/or energy transfer" most generally refers to a process in which an electron and/or energy is transferred from one molecular system to another or from one molecular moiety to another in the same molecule employing any type of mechanism. In particular, photo-induced electron transfer (PET) or Internal Charge Transfer (ICT) may be used as the approaches for the detection and quantification of the electrophiles in the sample.

The π-conjugated moiety and nucleophilic moiety are chosen so that an electron transfer can occur from the nucleophilic moiety to the π-conjugated moiety upon excitation which quenches the excited state of the π-conjugated moiety. The introduction of an electrophile which can bind to the nucleophilic moiety alters the oxidation potential of the π-conjugated moiety and so changes the conditions at which PET occurs.

In PET an electron is transferred from the highest occupied molecular orbital of a donor in its ground state to the highest occupied molecular orbital of an acceptor in its excited state. In the compounds described PET is arranged by coupling a nucleophile moiety (donor moiety) to a π-conjugated moiety (acceptor moiety) via a linker. The presence of the linker means that the π-conjugated moiety and the nucleophilic moiety are spatially distinct and any orbital interactions between these portions of the chemosensor or sensor constructed therefrom are minimized. The π-conjugated moiety is the site of both excitation and emission whereas the nucleophilic moiety is responsible for complexing to the electrophile.

In ICT, the nucleophilic moiety has electron donors and the π-conjugated moiety is linked by a conjugated bridge so as to form a single delocalized unit. The electron donor nucleophilic moiety pushes electron density into the system whilst the electron acceptor π-conjugated moiety pulls electrons from it. A more integrated structure, generally lacking a spacer, is required for a molecule to achieve ICT.

The term "sufficient time" or any lingual variation thereof refers to a period of time which would allow interaction between the electrophile in said sample and the nucleophile and the formation of an electrophile-bound chemosensor. The sufficiency of time may be determined based on prior experimentation using control samples of each component and monitoring the formation of the electrophile-bound chemosensor using various spectroscopic methods. Alternatively, the time period required for the formation of the electrophile-bound chemosensor may be determined based on a prior statistical evaluation which would provide an averaged time for the formation of the adduct under an experimental set of conditions. It should be stated that a person skilled in the art would be able to determine the sufficiency of time required for the formation of the complex without necessitating undue experimentation. One may perform the detection step at elevated temperatures, such as 50-100° C., in order to facilitate the reaction and shorten reaction times.

Contacting of the electrophile in the sample with the chemosensor or device may be achieved by one or more of various methods. In one embodiment, the chemosensor is dissolved in an aqueous or non-aqueous solvent and the resulting solution is brought into contact or exposed to a sample suspected of containing the electrophile.

In another embodiment, the chemosensor is immobilized on a solid or semi-solid support.

In another embodiment, the chemosensor is present in a gel or a matrix, in which case contact between the sample and the chemosensor may optionally require agitation of the sample, and/or additional time for the diffusion of electrophile to the chemosensor.

In any case, the chemosensor concentration must be sufficient to generate a detectable optical response in the presence of the electrophile.

The detection of the presence of at least one electrophile by way of detection of the electrophile-bound chemosensor may be achieved remotely by incorporation of the chemosensor as part of a fiber optic probe. In this embodiment of the invention, the chemosensor is attached to the fiber optic probe material, typically glass or functionalized glass (e.g., aminopropyl glass) or the chemosensor is attached to the fiber optic probe via an intermediate polymer, such as polyacrylamide. The observation of a detectable change in the optical properties of the chemosensor is optionally used in cases exposure to e.g., an environment containing a toxic electrophile is to be avoided.

Alternatively, the chemosensor may be kept separate from the device or the substrate until the detection of the electrophile is to take place, whereupon the chemosensor molecules are placed into the sample and then allow binding either to the sensor device or to the electrophile in the sample, thereafter binding to the device or substrate.

The detectable response may be quantified and used to measure the concentration of the electrophile in the environment. Quantification may be performed by comparison of the electromagnetic (e.g., optical) response to a standard or calibration curve. The standard curve may be generated according to methods known in the art using varying and known amounts of the electrophile in standard solutions.

As stated above, the chemosensor may be immobilized on a solid or semi-solid support. The solid support may be any solid substrate conventional in the art that supports an array and on which molecules are allowed to interact and their reaction detected without degradation of or reaction with its surface. The surface of the substrate may be a bead or particle such as microspheres or nano-beads, or planar glass, a flexible, semi-rigid or rigid membrane, a plastic, metal, or mineral (e.g., quartz or mica) surface, to which a molecule may be adhered. The solid substrate may be planar or have simple or complex shape.

Generally, the substrate according to the present invention may be composed of any porous material which will permit immobilization of an electrophile and which will not melt or otherwise substantially degrade under the conditions associated with the exposure to the electrophile. The surface to which the chemosensor, particularly a polymeric chemosensor, is adhered may be an external surface or an internal surface of the porous substrate.

The chemosensor may be mounted or loaded onto a solid or semi-solid surface in a variety of fashions. It can be spin coated or drop cast on silicon surface or absorbed on porous membrane or any other fashion. The device prepared thereby may be a part of a detecting unit which may be manufactured in accordance with the engineering and general knowledge known to a person skilled in the art. The chemosensor may be made to cover a plate or any part of a detector or a surface in close proximity to a detector which is made to measure the change in the optical properties, e.g., PET.

The polymeric chemosensors employed in the method and/or device of the invention may be constructed as nanotubes and may be used as such in the method and/or device.

The invention also pertains to a kit suitable for determining the identity of a molecule in a sample, the molecule having an electrophilic or nucleophilic moiety. Preferably, the kit includes directions for use. In one embodiment of the kit, the chemosensors are adhered to a solid support material, impregnated therein or in solution in an amount sufficient to react with the molecule in the sample.

In the alternative, the kit may include a solid support material coated with preferred chemosensors for contact with a sample suspected of comprising the molecule, wherein the solid support material may include, but not limited to, a non-aqueous matrix which may be a polysaccharide (such as agarose and cellulose); and other mechanically stable matrices such as silica (e.g. controlled pore glass), poly (styrenedivinyl)benzene, polyacrylamide, ceramic particles, optical fibers and derivatives of any of the above. In one embodiment, the solid support material comprises controlled pore glass beads retained in a column that is coated with preferred chemosensors that have high affinity for electrophilic or nucleophilic agents.

The kit may further include an illuminating source or a detection instrument, if the optical property change is not triggered by visible light or any changes that are not detectable in the visible range.

Those skilled in the art will appreciate that numerous changes and modifications may be made to the preferred embodiments of the invention and that such changes and modifications may be made without departing from the spirit of the invention. For example, by the implementation of known molecular recognition principles, the compounds disclosed herein can be modified to produce conducting polymers which are responsive to numerous electrophiles. It is therefore intended that the appended claims cover all such equivalent variations as fall within the true spirit and scope of the invention.

In order to understand the invention and to see how it may be carried out in practice, a preferred embodiment will now be described, by way of non-limiting example only, with reference to the accompanying drawings, in which:

In one embodiment of the method of the present invention, a chemosensor of the invention is an organic nucleophile, specifically N-(2-dimethylaminoethyl)-1,8-naphthalimide, referred to herein as Compound 1.

Compound 1 was found to be a highly selective and effective PET chemosensor that turned fluorescent on upon reacting with different electrophilic alkylating agents. The PET based sensing of such alkylating agents may be performed either in solutions or in the solid state. Compounds 1a to 1d, shown below, are non-limiting examples of electrophile-bond chemosensors derived from a reaction of Compound 1 with various electrophiles, namely, 1-halomethyl ethylether (compound 1a), 1-halothioethylether (compound 1b), dihalomethane (compound 1c) and halobenzyl (compound 1d).

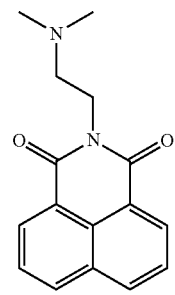

(1)

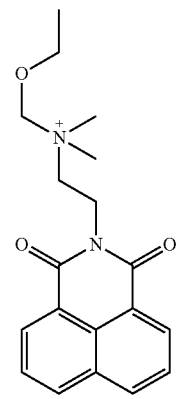

(1a)

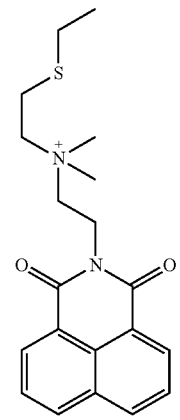

(1b)

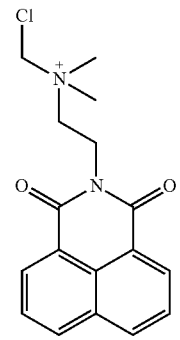

(1c)

(1d)

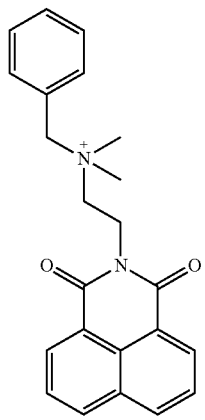

In the absence of protons and ligating metal ions, Compound 1 is a weak luminophore, emitting at around the red limit of the UV (382 nm in acetonitrile). Without wishing to be bound by theory, the exceptionally low emission is attributed to an efficient photo-induced electron transfer process (PET) that takes place between the photo-excited aromatic skeleton and the lone pair electrons of the free amine. In the presence of Lewis acids, such as acidic protons or ligating metal ions, the lone pair electrons of the free amine quencher are engaged in a hydrogen-nitrogen or metal-nitrogen bond. Once engaged in such a new bond with the Lewis acid, the former lone-pair of electrons of the amine group can no longer serve as an efficient quencher to the photo-excited aromatic skeleton since it is stabilized in the form of a □-bond. In this Lewis acid bound state Compound 1 is a highly luminescent species.

The reaction between an organic nucleophile such as compound 1 and one or more alkylating agent is not limited to solutions and could also be performed very efficiently when in the solid phase with, for example, compound 1 adsorbed on a filter paper, as will be exemplified below.

The chemosensor molecules employed by the method of the invention may be prepared according to known methodologies. Generally, the compounds of general formula I may be constructed from the basic acenaphthene system or from a commercially available naphthalimide, as demonstrated herein next.

The polymers and/or oligomers employed may be used by employing one or more methodologies known in the art for their synthesis (For example see *Resins for Coatings*, Stoye and Freitag, Eds., New York, 1996).

A person skilled in the art would have the necessary knowledge to derivatize a known or commercially available compound in order to produce a more effective chemosensor. The analysis of the compounds may be carried out by any one standard method of analysis, such as thin layer chromatography (TLC), gel electrophoresis, high performance liquid chromatography (HPLC) and mass spectrometry (MS), used by those of skill in the art to assess, e.g., the purity, and chemical or physical properties of the chemosensor.

Methods for purification of the chemosensors to produce substantially pure compounds are known to those of skill in the art. A substantially chemically pure compound may, however, be a mixture of stereoisomers. In such instances, further purification might increase the specific activity of the compound.

Example 1

Solid State Sensing of Alkylating Agents Using N-(2-dimethylaminoethyl)-1,8-naphthalimide (Compound 1)

A filter paper (Whatman) was dipped in a solution of the Compound 1 (20 mg/mL) in acetonitrile for 1 min. The filter paper was left to dry in the dark, then placed in a Teflon holder. The Teflon holder was fitted into one of two ground joints of a round-bottomed flask. The second joint was fitted with a tube that contained calcium chloride beads. The Teflon holder was connected to a vacuum pump that aspirated the atmosphere of the flask through the filter paper. The experiment was performed by placing the relevant alkylating agent (selected from chloroethylmethyl ether, chloroethylmethyl thioether, dichloromethyl or benzyl chloride), in the amount of 10 mg each and $Na_2CO_3$ (10 mg) at the bottom of a two-necked round-bottomed flask, then allowing the system to equilibrate for about 30 min and then aspirating the atmosphere of the flask for different periods of time.

Upon drying, the filter paper turned very weakly luminescent (□$_{ex}$=366 nm) in the blue region. Exposure for several seconds of the filter paper that was loaded with Compound 1 to the atmosphere above a one-drop (ca. 50 μL) mixture of the mustard analog, chloromethyl ethylether, and 10 mg of sodium carbonate, resulted in a dramatic increase in the luminescence and a red shift in its color.

Similar control experiments that were performed with hydrochloric acid and with different metal ions did not change the luminescence of the filter paper because of the presence of the base (or acid) and low vapor pressure (ions).

FIG. 1 and FIG. 2 represent the resulting absorption and fluorescence spectra (respectively) of the reaction of Compound 1 with the different alkylating agents.

FIG. 1 depicts the absorption and emission spectra of Compound 1 in acetonitrile in the presence of triethylamine and increasing concentrations of chloromethyl ethyl ether as the electrophile. As can be appreciated from FIG. 1, the absorption spectrum of Compound 1 is practically insensitive to the addition of the electrophile. In contrast, the presence of the electrophile turns the luminescence on. At saturation, the luminescence is about 130 times stronger than that of free Compound 1.

Saturation occurs at around a 1:1 ratio between the electrophile Compound 1, as shown in FIG. 2. This gives an indication to an efficient reaction that proceeds to completion even at rather low concentrations, allowing efficient detection of micromolar concentrations of electrophiles in solutions. Similar results were obtained with other alkylating agents of similar or different electrophilicity. Dichloromethane, a rather weak electrophile, was found to react with Compound 1 and turned its luminescence on.

Example 2

Synthesis of 4,6-dietoxy-1,8-naphthalimide (Compound 2)

The synthesis of Compound 2 having both a luminescent moiety (dietoxy-1,8-naphthalimide) and a nucleophilic moiety (1,1-dimethyl alkyl amine) was undertaken in 5 synthetic steps (a-e) as detailed herein below and in Scheme 1.

Step (a)-5,6-Dibromoacenaphthene [Ref. 5]

A suspension of N-bromosuccinimide (NBS) (25 gr, 143 mmol) in DMF (50 ml) was added in portions to an ice-cooled suspension of acenaphthene (10 g, 65 mmol) in DMF (15 mL) over a period of 1 h. The temperature of mixture was not allowed exceed 15° C. The mixture was stirred for a further 12 h and then allowed to warm to room temperature. The precipitate was filtered with suction, washed with ethanol (3×50 mL), and purified by stirring over night in refluxing ethanol (200 ml). Cooling to room temperature, filtration, washing with ethanol, and drying in vacuo yielded 4.5 g (22%) of a beige crystalline solid (m.p. 169-172° C.) that was suitable for further work.

$^1$H NMR: δ 3.28 (s, 4H; H-1,2), 7.06 (d, 3J=7.49 Hz, 2H; H-3,8), 7.76 ppm (d, 3J=7.49 Hz, 2H; H-4,7);

$^{13}$C NMR (68 MHz, CDCl$_3$): δ 29.99 (C-1,2), 114.31, 120.87, 131.80, 135.77, 141.75, 147 ppm (arom-C).

Step (b)-1,8-Dibromoacenaphthenedione [Ref. 6]

1,8-Dibromoacenaphthene (8 g, 25.6 mmol) was dissolved in acetic anhydride (0.5 L) at 110° C. CrO$_3$ (20.4 g, 205 mmol) was added carefully to the stirred solution over a period of 2 h. The resulting green suspension was stirred at 160° C. for 30 min., and then poured while hot onto crushed ice (1 kg). Concentrated HCl (20 mL) was added and the mixture was filtered. The brownish precipitate was washed with water, dried in vacuo and recrystallized from acetic anhydride (2 L).

1,8-Dibromoacenaphthenedione (6.33 g, 73%) was obtained as a light brown solid, m.p. 239° C.

Elemental analysis—C$_{12}$H$_4$Br$_2$O$_2$ (340.0): calcd. C, 42.40; H, 1.19. found C, 42.22; H, 1.19. 2.

$^1$H NMR (CDCl$_3$): δ 57.93 (d, J=7.6 Hz, 2H, H$_{4,7}$), 8.27 (d, J=7.6 Hz, 2H, H$_{3,8}$).

Step (c)-1,8-Dibromonaphthoic Anhydride 1,8-Dibromoacenaphthenedione (6.33 g, 18.6 mmol) was dissolved in a mixture of 1,4-dioxane (400 mL) and NaOH (2 M, 400 mL) and heated to 100° C. A solution of H$_2$O$_2$ (10%, 400 mL) was added slowly to the stirred solution. After stirring for a further 30 min. at 100° C., the mixture was cooled to room temperature and filtered. The filtrate was acidified with concentrated HCl producing a voluminous precipitate. This was separated by centrifugation, washed twice with water and dried in vacuo. 1,8-dibromonaphthoic anhydride was obtained as a light brown powder, m.p. 260° C.

Elemental analysis: C$_{12}$H$_4$Br$_2$O$_3$ (356.0): calcd. C, 40.49; H, 1,13. found C, 40.45; H, 1.11.2.

$^1$H NMR ([D$_6$] acetone): δ 5 7.95 (d, J=7.5 Hz, 2H, H$_{5,8}$), 8.17 (d, J=7.5 Hz, 2H, H4,9).

Step (d)-4,6-dibromo-1,8-naphthalimide [Ref. 7]

4,6-dibromo-1,8-naphthalic anhydride (0.86 g, 2.4 mmol) and N,N-dimethylethylenediamine (0.53 ml, 4.8 mmol) were added to 10 mL ethanol, the reaction mixture was stirred at reflux temperature for 2 h, then cooled, filtered, and dried, the crude product was obtained as yellow solid (0.3 g, 30%).

Step (e)-4,6-dietoxy-1,8-naphthalimide (Compound 2) [Ref. 8]

(0.3 gr, 0.7 mmol) of 4,6-dibromo-1,8-naphthalimide, 52 mg of CuBr, and a 10:1 stoichiometric ratio of sodium ethoxide in 20 ml ethanol, sodium (0.164 gr, 7 mmol) were stirred and refluxed for 18 h. Ethanol was removed by distillation. Crude product was purified by silica gel. The reaction afforded a tan or yellow powder (0.27 gr, 100%).

Example 3

Solid State Sensing of Chlorodiethyl Thioether Using N-(2-dimethylaminoethyl)-4,6-diethoxy-1,8-naphthalimide (Compound 2)

The ability of Compound 2 in sensing chlorodiethyl thioether was tested similarly to the procedure detailed in Example 1 above. The reaction between the electrophile and the chemosensor is depicted in Scheme 2.

As FIG. 3 demonstrates, the presence of the electrophile turns caused a marked change in the emission spectrum of the chemosensor molecule designated Compound 2. In the absence of the electrophile, the emission was substantially quenched.

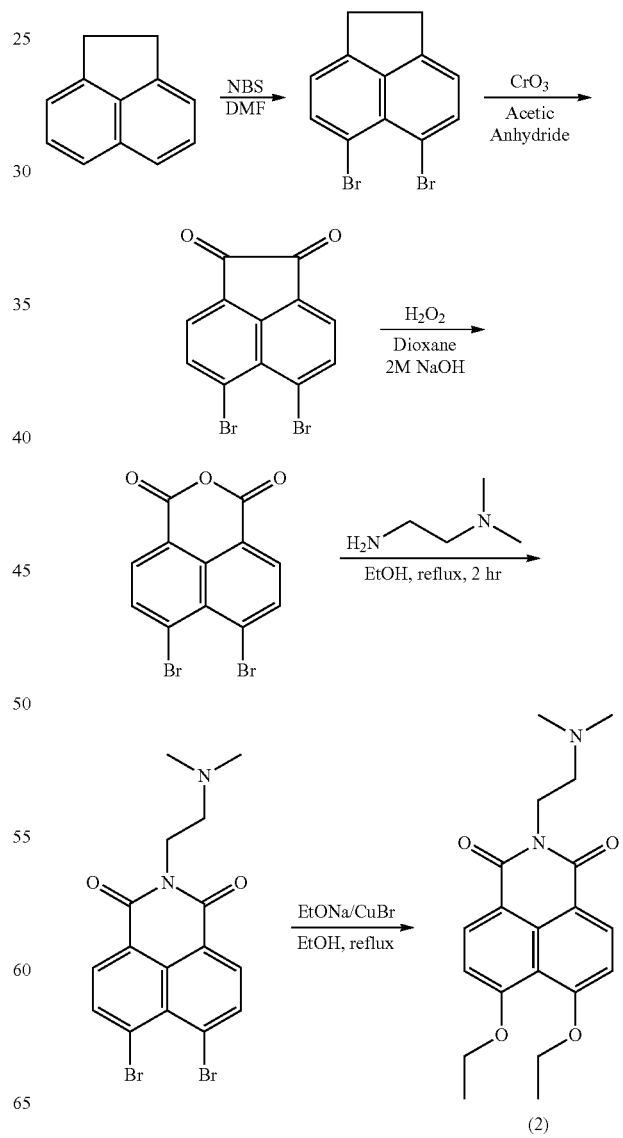

Scheme 1

Scheme 2

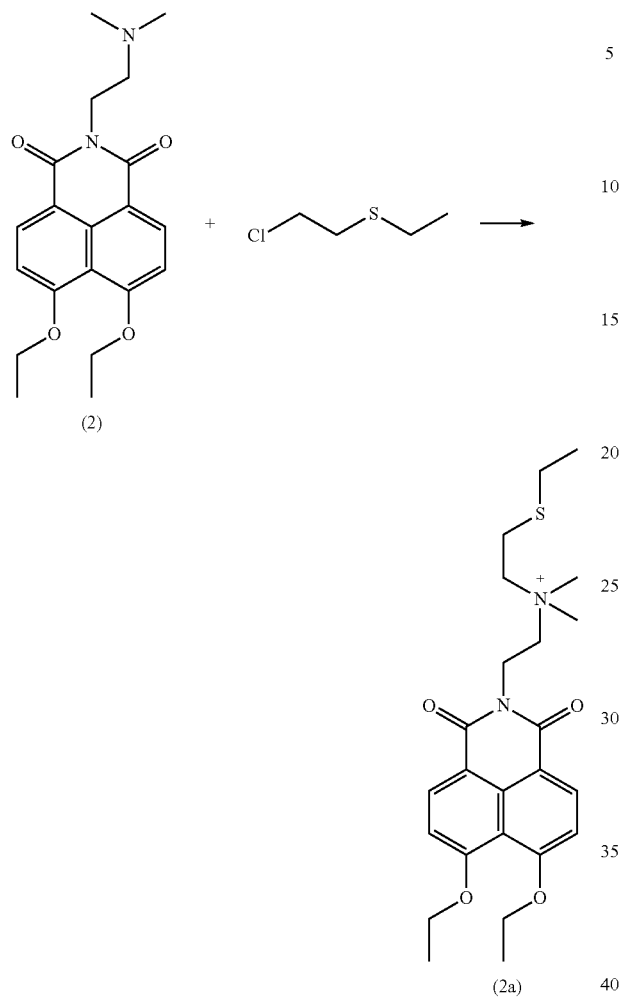

Example 4

Identification of Alkylating Agents

As shown in FIG. 4, nine chemosensors of the invention (top row) were absorbed on Whatman filter paper. Before exposure to eight different alkylating agents (left-most column) their emission spectra and levels were measured (second from top row) after being excited from a 365 nm light source.

Materials

Referring to the chemosensors shown in FIG. 4 (from left to right), they were made as follows;

Starting materials—5,5'-Bis(tri-n-butylstannyl)-2,2'-bithiophene (Wei, Y.; Yang, Y.; Yeh Ming, *J. Chem Mater*, 1996, 8, 2659-2666); 2,7-Diformyl-9,9-di-n-octylfluorene (W. Wang, J. Xu, Y-H Lai, F. Wang; *Maromulecules*, 2004, 37, 3546-3553; Poly[9,9'-dioctylfluoren-2,7-ylenevinylene-co-alt-5,5'-(2,2'-bipyridylenevinylene)] (Liu, B.; Yu Lin W.; Pei, J.; Liu Yong S.; Yee Hing L.; Huang W., *Maromulecules*, 2001, 34, 7932-7940).

3-(4-pyridyl)-thiophene (Chemosensor 5)

To a solution of 4-Bromo pyridine hydrochloride (1.23 g, 6.32 mmol) in DME/H$_2$O (82 ml/22 ml) (6:1.7) was added Pd(PPh$_3$)$_4$ (0.35 g, 3.12 mmol), Ba(OH)$_2$.8H$_2$O (4.98 g, 9.49 mmol) and Thiophene-2-boronic acid (0.89 g, 6.97 mmol). The mixture was stirred overnight at 85° C. After cooling to room temperature, the reaction mixture was extracted with dichloromethane. The combined organic layers were washed with water and brine and then dried over sodium sulfate. After filtration, the solvent was evaporated. The crude product was purified by column chromatography (silica, Methanol: Dichloromethane=1:99, v/v) and dried under vacuum to give 3-(4-pyridyl)-thiophene as white solid (1.7 g, 75%). $^1$H NMR (300 MHz, CDCl$_3$): δ 7.43 (d, 2H), 7.45 (d, 2H), 7.64 (dd, 1H), 8.69 (d, 2H). $^{13}$C NMR (500 MHz, CDCl$_3$): δ 120.73, 123.05, 125.63, 127.06, 139.41, 142.54, 150.34. M.P.=138° C. M.S.: (CI) 162, M+H$^+$; 161, M$^+$.

2-bromo-3(4-pyridyl)-thiophene

Zhang, Y.; Homfeldt, A. B.; Gronovicz, S., *J. Het. Chem.*, 1995, 32, 435.

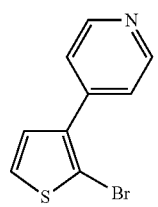 [SMILES: Brc1sccc1-c1ccncc1]

To a solution of 3-(4-pyridyl)-thiophene (1.6 g, 10 mmol) in acetic acid (50 ml) was added dropwise a solution of N-bromosuccinimide (2.7 g, 15 mmol) in acetic acid (100 ml) and the mixture was allowed to react for 2 h at room temperature. The mixture was washed with saturated aqueous potassium carbonate solution. The reaction mixture was extracted three times with dichloromethane and then dried over sodium sulfate and filtered. After removal of the solvent, the residue was purified by column chromatography using (silica, hexane:ethylacetate=20:80, v/v) to afford a yellowish solid. (0.53 g, 38%). $^1$H NMR (300 MHz, CDCl$_3$): δ 7.03 (d, 1H), 7.33 (d, 1H), 7.46 (d, 2H), 8.63 (d, 2H). $^{13}$C NMR (500 MHz, CDCl$_3$) δ 123.00, 126.78, 128.28, 130.84, 138.12, 142.61, 149.69. M.P.=57 C M.S.: (CI) 139, 141, M$^+$.

3,3'-bis(4-pyridyl)-2,2'-bithiophene

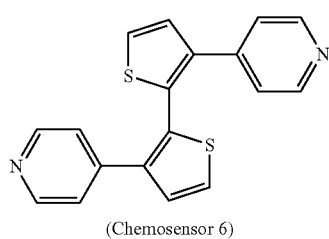 [SMILES: c1cc(-c2ccsc2-c2sccc2-c2ccncc2)ccn1]

(Chemosensor 6)

A solution of anhydrous NiCl$_2$ (0.65 g, 5 mmol) and triphenylphosphine (5.24 g, 20 mmol) in DMF (25 ml) was stirred at 80° C. under N$_2$ until received homogenous blue solution. To the solution was added zinc powder (0.32 g, 5 mmol) after the mixture was stirred at 80° C. for approximately 1 h until the mixture turn red, 2-bromo-3-(4-pyridyl)-thiophene (0.96 g, 4 mmol) was added and the mixture was stirred overnight at 80° C. The resulting mixture was washed with aqua solution of ammonia and was extracted with dichloromethane and then dried over sodium sulfate and filtered. After removal of the solvent, the residue was purified by column chromatography using (alumina, hexane:ethylacetate=50:50, v/v) to afford a yellowish solid. (0.77 g, 60%). $^1$H NMR: (300 MHz, CDCl$_3$): δ 6.72 (dd, 4H), 7.07 (d, 2H), 7.45 (d, 2H), 8.27 (dd, 4H). $^{13}$C NMR (500 MHz, CDCl$_3$) δ 122.58, 127.29, 128.73, 138.43, 143.11, 160.88 M.S.: (+DCI) 321.1, M+H$^+$; 321, M$^+$.

3,3'''-bis(4-pyridyl)-[2,2'; 5',2''; 5'',2''']-Quaterthiophene

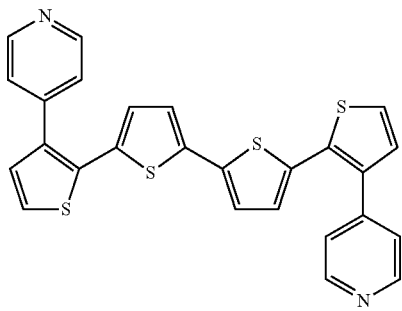

(Chemosensor 7)

2-bromo-3-(4-pyridyl)-thiophene (0.2 g, 0.8 mmol) and 5,5'-Bis-tributyltin-[2,2']-bithiophene (0.24 g, 0.32 mmol) were dissolved in dry toluene (20 ml) under N$_2$. To the solution was added Pd(PPh$_3$)$_4$ (0.03 g, 0.03 mmol). The mixture was reflux for 48 h. The mixture was cooled to room temperature and evaporate. The residue was purified by column chromatography using (alumina, Methanol:Dichloromethane=0.5:95.5, v/v) to afford an orange solid (0.12 g, 77%).

$^1$H NMR: (300 MHz, CDCl$_3$): δ 6.77 (d, 2H), 6.90 (d, 2H), 7.06 (d, 2H), 7.40 (d, 2H), 8.56 (d, 2H). $^{13}$C (500 MHz, CDCl$_3$) 90.07, 93.78, 123.79, 124.26, 125.51, 128.08, 129.78, 143.82, 150.08, 162.77, M.P.=197.5 C MS: MALDI-TOF [M$^+$] m/z 484.0.

2,5-dibromo-3(4-pyridyl)-thiophene

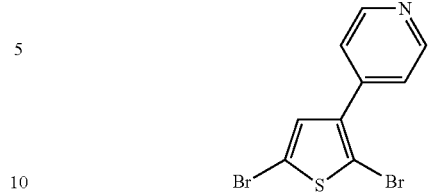

To a solution of 3-(4-pyridyl)-thiophene (1.6 g, 10 mmol) in acetic acid (50 ml) was added a solution of N-bromosuccinimide (4.4 g, 24 mmol) in acetic acid (100 ml) and the mixture was allowed to react over night at room temperature. The mixture was washed with saturated aqueous potassium carbonate solution. The reaction mixture was extracted three times with dichloromethane and then dried over sodium sulfate and filtered. After removal of the solvent, the residue was purified by column chromatography using (silica, hexane:ethylacetate=25:70, v/v) to afford a white solid. (1.9 g, 60%). $^1$H NMR (300 MHz, CDCl$_3$): δ 7.03 (d, 1H), 7.33 (d, 1H), 7.46 (d, 2H), 8.63 (d, 2H). $^{13}$C NMR (500 MHz, CDCl$_3$) δ 123.00, 126.78, 128.28, 130.84, 138.12, 142.61, 149.69. M.P.=57 C M.S.: (CI) 139, 141, M$^+$.

4-[2,2'; 5',2'']terthiophene-3'-yl-pyridine

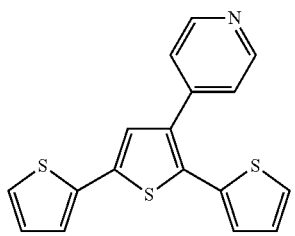

(Chemosensor 3)

2,5-dibromo-3-(4-pyridyl)-thiophene (0.23 g, 0.7 mmol) and 2-tributyltin-thiophene (0.57 g, 1.5 mmol) were dissolved in dry toluene (20 ml) under N$_2$. To the solution was added Pd(PPh$_3$)$_4$ (0.07 g, 0.07 mmol). The mixture was reflux for 48 h. The mixture was cooled to room temperature and evaporate. The residue was purified by column chromatography using (silica ethyl acetate:hexane=20:80, v/v) to afford a yellowish powder (0.18 g, 80%).

NMR: $^1$H (CDCl$_3$): δ 6.98-7.00 (dd, 2H), 7.05-7.06 (dd, 1H), 7.17 (s, 1H), 7.22-7.23 (dd, 1H), 2.87 (s, 4H), 7.27-7.28 (dd, 2H), 7.30-7.31 (dd, 2H), 8.47-8.51 (dd, 2H). $^{13}$C (CDCl$_3$) δ 125.6, 126.1, 126.9, 127.6, 128.5, 129.2, 129.4, 129.8, 136.2, 138.0, 138.3, 138.6, 145.5, 151.8. MS: MALDI-TOF [M$^+$] m/z 325.0, mp 91.34.

3,5-Dithiophen-2-yl-pyridine

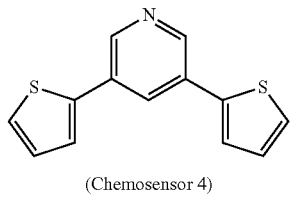 [SMILES: c1csc(-c2cncc(-c3cccs3)c2)c1]

(Chemosensor 4)

3,5-dibromo-pyridine (0.3 g, 1.2 mmol) and 2-tributyltin-thiophene (1.2 g, 3 mmol) were dissolved in dry toluene (20 ml) under N$_2$. To the solution was added Pd(PPh$_3$)$_4$ (0.13 g, 0.1 mmol). The mixture was reflux for 48 h. The mixture was cooled to room temperature and evaporate. The residue was purified by column chromatography using (silica ethyl acetate:hexane=25:75, v/v) to afford a yellowish powder (0.18 g, quantitative yield).

NMR: $^1$H(CDCl$_3$): δ 7.08-7.11 (t, 2H), 7.32-33 (dd, 2H), 7.34-7.35 (d, 2H), 7.95 (s, 1H), 8.72 (s, 2H). $^{13}$C(CDCl$_3$) δ 126.4, 128.1, 130.2, 131.8, 132.3, 141.8, 147.4. MS: MALDI-TOF [M$^+$] m/z 244.1, mp. 151.64.

1,4-Di(2'-ethylhexyloxy)benzene

Hsu, M. A.; Chow, T. J., *Aust. J. Chem,* 2002, 55, 499-504

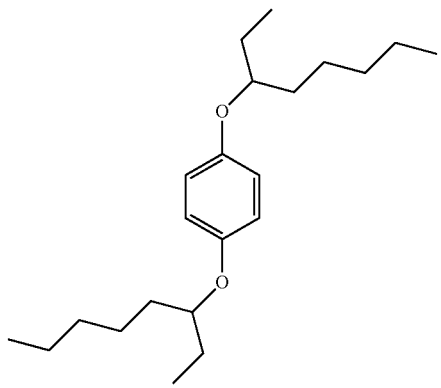 [SMILES: CCCCCC(CC)Oc1ccc(OC(CC)CCCCC)cc1]

A solution of hydroquinone (17.6 g, 0.16 mol) and KOH (25.6 g, 0.457 mol) was added. The mixture was heated overnight under a nitrogen atmosphere. The precipitates were filtered after being cooled. The filtrate was concentrated, and was passed through silica gel chromatographic column eluted with ethyl acetate:hexane (1:10, v/v) to yield a colorless 1,4-Di(2s-ethylhexyloxy)benzene in 78% yield.

NMR: $^1$H(CDCl$_3$): δ 0.92 (m, 12H), 1.33-1.69 (m, 16H), 1.71 (m, 2H), 3.81 (d, 4H), 6.84 (S, 4H). $^{13}$C(CDCl$_3$) δ 11.32, 14.29, 23.29, 24.10, 29.33, 30.78, 39.72, 71.45, 115.61, 153.70 M.S.: (+EI) 334.

2,5-Di(bromomethyl)-1,4-di(2'-ethylhexyloxy)benzene

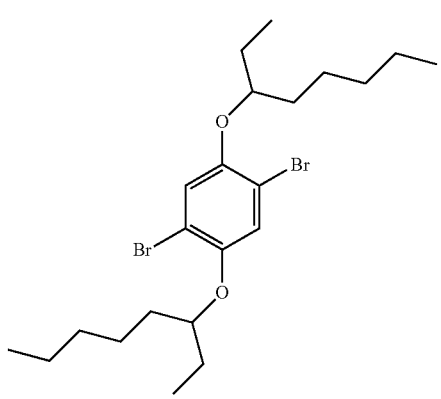 [SMILES: CCCCCC(CC)Oc1cc(Br)c(OC(CC)CCCCC)cc1Br]

To a round-bottomed flask containing 1,4-Di(2'-ethylhexyloxy)benzene (20, 60 mmol) and paraformaldehyde (4 g, 130 mmol) in acetic acid (50 ml) was added a solution of HBr (33% in acetic acid, 26 ml, 150 ml). The mixture was stirred at 100° C. for 8 h, while a white precipitate formed. The mixture was poured into distilled water, and the precipitate was collected by filtration. The precipitate was dissolved in dichloromethane, and the solution was washed with saturated NaHCO$_3$. The organic layer was separated, dried over Na$_2$SO$_4$ and concentrated under vacuum. The residue was recrystallized from dichloromethane:methanol to give a white solid 2,5-Di(bromomethyl)-1,4-di(2'-ethylhexyloxy)benzene (25 g, 80%).

1,4-Di(2'-ethylhexyloxy)-2,5-bis-(triphenylphosphino)methyl]-benzene Dibromide

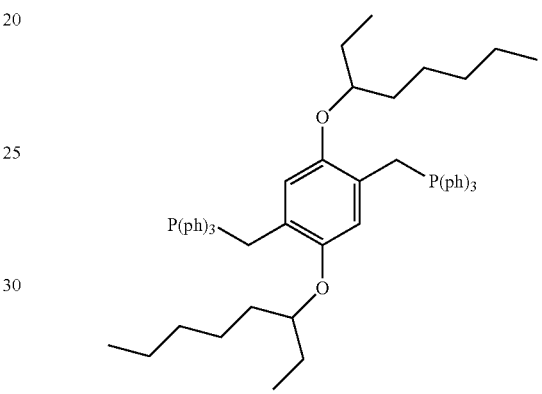

To a flask was added 2,5-Di(bromomethyl)-1,4-di(2'-ethylhexyloxy)benzene (5.2 g, 10 mmol) and triphenyl phosphine (5.8 g, 22 mmol) under a nitrogen atmosphere. To this was added freshly distilled DMF (40 ml) and the resulting solution was heated reflux for 2 h. The solution was cooled and poured dropwise into ether, which was vigorously stirred. A white precipitate formed and was collected by filtration. It was dried under vacuum to give a white solid (10.2 g, 80%).

Poly[1,4-di(2'-ethylhexyloxy)benzene-ylenevinylene-co-alt-5,5'-(2,2'-bipyridylenevinylene)]

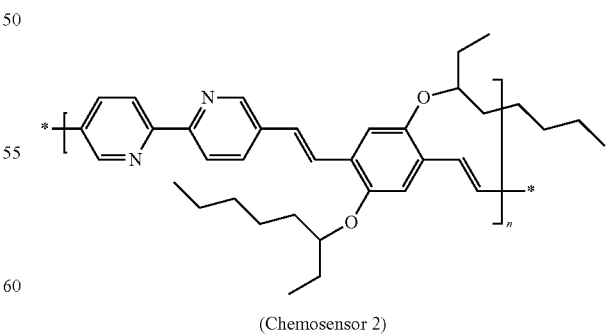

(Chemosensor 2)

To a solution of 2,2'-bipyridine-5,5'-dialdehyde (0.1 g, 0.47 mmol) and 1,4-Di(2'-ethylhexyloxy)-2,5-bis-(triphenylphosphino)methyl]-benzene Dibromide (0.49 g, 0.47 mmol) in 30 ml CH$_2$Cl$_2$ was added dropwise with stirring NaOEt 0.025 g in 8 ml Ethanol. The mixture was stirred for three days at room temperature. The mixture was added to methanol (300 ml) the precipitate was collected by filtration. The residue was purified by column chromatography using (silica, MeOH:dichloromethane=5:95, v/v) to afford a red solid (300 mg, 30%).

NMR: $^1$H(CDCl$_3$): δ 0.87 (br, 6H), 0.89 (br, 4H), 1-1.2 (m, 16H), 1.22 (m, 2H), 2.87 (s, 4H), 5.24 (m, 4H), 7.17 (br. ph), 7.49-7.7 (m, vinyl-H), 7.98 (pyridyl), 8.44 (pyridyl), 8.80 (pyridyl). GPC: Mn=2480 g/mol

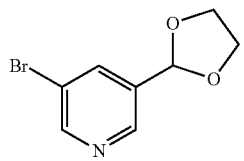 [SMILES: Brc1cncc(C2OCCO2)c1]

3-bromo-5-[1,3]-dioxolan-2-yl-pyridine

5-Bromo-3-pyridine-carboxaldehyde (1.5 g, 8 mmol), ethylene glycol (0.6 ml, 10 mmol) and a catalytic amount of camphor sulphonic acid in 50 ml benzene. The reaction was done in a Dean Stark apparatus and stirred over night at 120° C. The solvent was removed in a vacuum and the reactant was dissolved in dichloromethane and washed with water, extracted with dichloromethane, dried over Na$_2$SO$_4$ and the solvent was removed in a vacuum to give a colorless oil. (1.84 g, quantitative yield).

NMR: $^1$H(CDCl$_3$): δ 4.01 (m, 4H), 5.77 (s, 1H), 7.88 (s, 1H), 8.54 (d, 1H), 8.6 (d, 1H). $^{13}$C(CDCl$_3$) δ 65.13, 100.64, 120.31, 135.25, 136.43, 146.10, 151.10. CI-MS-[M$^+$] m/z 230.

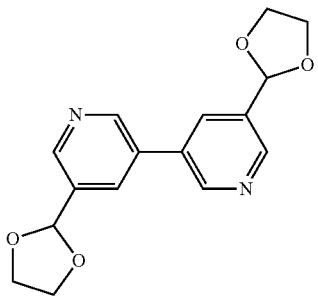 [SMILES: c1ncc(C2OCCO2)cc1-c1cncc(C2OCCO2)c1]

5,5-Bis-[1,3]-dioxolan-2-yl-[3,3']bipyridinyl

A solution of anhydrous NiCl$_2$ (1.3 g, 10 mmol) and triphenylphosphine (10.4 g, 40 mmol) in DMF (50 ml) was stirred at 80° C. under N$_2$ until received homogeneous blue solution. To the solution was added zinc powder (0.65 g, 10 mmol) after the mixture was stirred at 80° C. for approximately 1 h until the mixture turn red, 3-bromo-5-[1,3]-dioxolan-2-yl-pyridine (2.3 g, 10 mmol) was added and the mixture was stirred overnight at 80° C. The resulting mixture was washed with aqua solution of ammonia and was extracted with dichloromethane and then dried over sodium sulfate and filtered. After removal of the solvent, the residue was purified by column chromatography using (alumina, hexane:ethylacetate=20:80, v/v) to afford a white solid (1.8 g, 60%).

$^1$H NMR: (300 MHz, CDCl$_3$): δ 4.01 (m, 8H), 5.80 (s, 2H), 7.89 (s, 1H), 8.54 (d, 1H), 8.70 (d, 2H), 8.79 (d, 2H). $^{13}$C (500 MHz, CDCl$_3$) δ 65.51, 101,72, 116.73, 132.69, 134.01, 145.93, 147.98. CI-MS− [M−H$^+$] m/z 301. M.P.=130 C

[3,3']-bipyridinyl-5,5' dicarbaldehyde

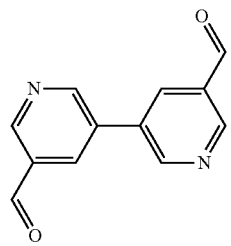 [SMILES: O=Cc1cncc(-c2cncc(C=O)c2)c1]

HCl (10 ml, 7M) was gradually added to the solution of 5,5-Bis-[1,3]dioxolan-2-yl-[3,3]bipyridinyl (0.8 g, 2.6 mmol) in 20 ml CHCl$_3$. The mixture was stirred at room temperature for 24 h. The organic layer was separated, washed with saturated solution of potassium carbonate and dried over sodium sulfate. The solvent was evaporated to afford a white solid in quantitative yield, 0.55 g.

NMR: $^1$H (CDCl$_3$): δ 8.36 (s, 2H), 9.08 (d, 4H), 10.18, (s, 2H). $^{13}$C(CDCl$_3$) δ 133.84, 152.04, 152.91, 189.94. M.P.>200° C., (MS-CI), [M+NH$_4$] m/z 230, [M+H$^+$] m/z 21

2-Hydroxymethyl-9,9-dioctylfluorene

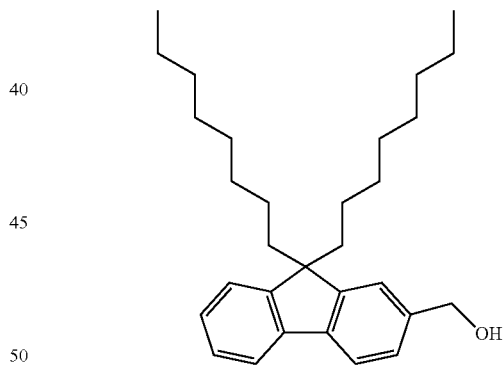

A mixture of the 9,9-Dioctylfluorene-2-aldehyde (1.2 g, 2.8 mmol) and sodium borohydride (0.085 g, 2.8 mmol) in THF (40 ml) was stirred at room temperature for 24 h. The mixture was treated with concentrated HCl-water (1:1) until the resultant solution was slightly acidic. The aqueous layer was saturated with NaCl and extracted with dichloromethane. The organic layers were combined, dried with Na$_2$SO$_4$, and evaporated under reduced pressure to give white solid (95%,1.1 g).

NMR: $^1$H (CDCl$_3$): δ 0.54 (t, 6H), 0.78 (t, 6H), 1.03-1.13 (m, 16H), 1.78 (m, 2H), 1.90 (t, 4H), 4.71 (s, 2H), 7.23-7.27 (m, 5H), 7.63 (dd, 2H). $^{13}$C(CDCl$_3$) δ 14.54, 23.09, 24.30, 29.71, 30.53, 32.28, 40.82, 55.54, 66.30, 120.20, 122.06, 126.27, 140.29, 140.93, 151.88. MS: MALDI-TOF [M$^+$] m/z 420.35.

33
2-Chloromethyl-9,9-dioctylfluorene

34
2(9,9-Dioctyl-9H-fluorenyl)methyl-triphenyl-phosphonium chloride

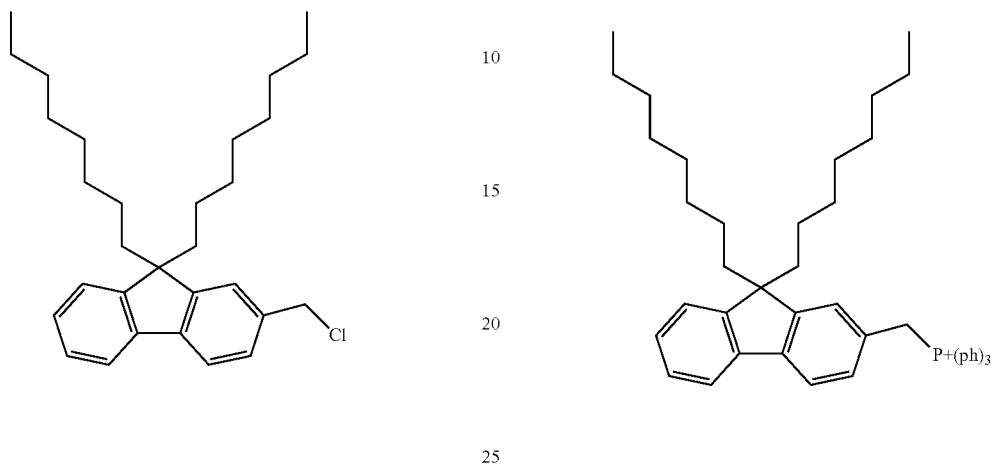

To a solution of (9,9-Dioctyl-9H-fluoren-2-yl)-methanol (0.3 g, 0.07 mmol) in dichloromethane (5 ml) was added dropwise thionyl chloride (0.1 ml, 1 mmol). The mixture was stirred for 3 h at room temperature and then washed three times 50 ml of water. The aqueous layer was extracted with 50 ml of dichloromethane. The combined organic were washed with dilute aqueous $NaHCO_3$ solution, dried over $Na_2SO_4$, and evaporated under reduced pressure to give white solid (85%, 0.25 g).

NMR: $^1$H (CDCl$_3$): δ 0.54-0.57 (m, 4H), 0.73-0.77 (m, 6H), 1.03-1.10 (m, 16H), 1.12-1.15 (m, 4H), 1.85-191 (m, 4H), 4.6 (s, 2H) 7.24-7.28 (m, 3H), 7.59-7.61 (m, 1H), 7.63-7.64 (m, 2H). $^{13}$C(CDCl$_3$) δ 14.0, 22.5, 23.60, 29.1, 29.13, 29.8, 31.7, 40.1, 46.8, 55.1, 119.9, 123.2, 127.5, 136.5, 140.7, 151.6. MS: MALDI-TOF [M$^+$] m/z 665.47.

A mixture of 2-Chloromethyl-9,9-dioctyl-9H-fluorene (0.2 g, 0.5 mmol) and triphenyl phosphine (0.054 g, 2 mmol) in DMF (35 ml). The mixture was stirred for 5 h in 100° C. The reactant was cooled to room temperature and added slowly to 200 ml ether while stirring. The white solid was filtered, washed with ether. It was dried under vacuum to give a white solid (0.28 g, 80%).

NMR: $^1$H(CDCl$_3$): δ 0.68 (m, 4H), 0.68-0.72 (t, 6H), 0.82 (m, 8H), 0.97-1.1 (m, 12), 1.7 (m, 2H) 1.75 (m, 2H), 5.19 (d, 2H), 6.83-6.84 (d, 1H), 6.9 (dd, 1H), 7.18-7.19 (m, 2H), 7.53-7.59 (m, 12H), 7.66-7.69 (m, 3H). $^{13}$C(CDCl$_3$) δ 14.10, 22.88, 24.50, 29.49, 29.70, 30.36, 31.93, 41.72, 43.98, 45.21, 126.82, 127.66, 128.29, 128.35, 128.45, 128.85, 128.89, 130.63, 138.01, 141.01, 147.87.

5,5is-[2-(9,9-dioctyl-9H-fluoren-2-yl)-vinyl]-[3,3]bipyridinyl

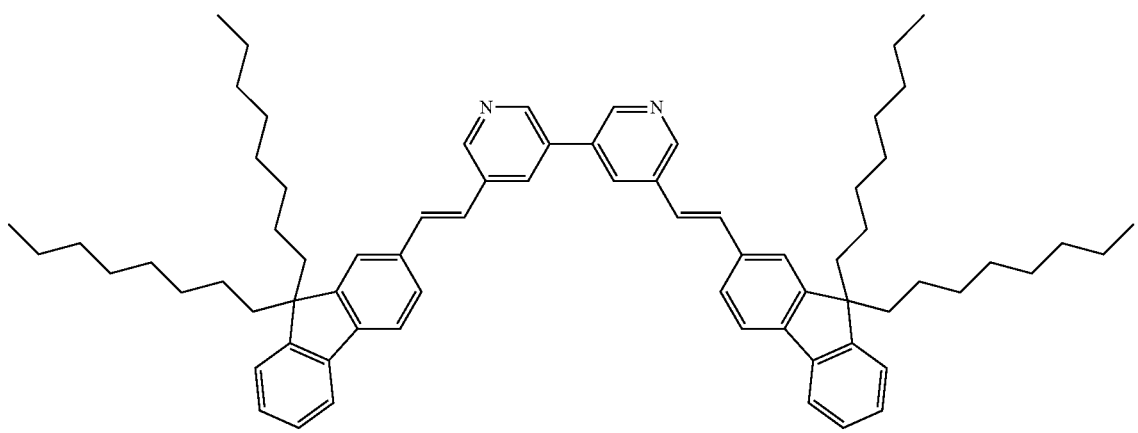

(Chemosensor 9)

To a solution of 2-(9,9-Dioctyl-9H-fluorenyl)methyl-triphenyl-phosphonium chloride (0.25 g, 0.35 mmol) in 5 ml ethanol and [3,3]-bipyridinyl-5,5'-dicarbaldehyde (0.046 g, 0.01 mmol) in 10 ml $CH_2Cl_2$ was added dropwise with stirring NaOEt (0.005 g, 0.23 mmol) in 5 ml Ethanol. After 2 hr of stirring the solvent was evaporated in vacuum and was passed through alumina chromatographic column eluted with ethyl acetate:hexane (20:80, v/v) to yield a yellow powder in 50% yield.

NMR: $^1H(CDCl_3)$: 0.55 (t, 6H), 0.82 (m, 16H), 1.07-1.18 (m, 16H), 1.22 (m, 2H), 2.79 (m, 2H), 3.67 (s, 2H), 3.74 (s, 1H), 5.13-5.18 (d, 2H), 6.45 (dd, 2H), 6.61-6.67 (d, 2H), 6.82 (d, 1H), 7.06 (d, 2H), 7.33 (d, 1H), 7.66 (m, 12H), 7.69 (t, 3H). $^{13}C$ $(CDCl_3)$ δ 15.80, 24.8, 25.60, 30.07, 31.0, 32.1, 72.5, 115.9, 119.8, 120.4, 125.4, 129.5, 131.8, 136.1, 136.6, 152.1, 160.4. M.S.: MALDI-TOF [M$^-$-PPh$_3$] m/z 480.33.

{2,5-Bis-(2-ethyl-hexyloxy)-4-[2-(4-methoxy-phenyl)-vinyl]-benzyl}-triphenyl-phosphonium bromide

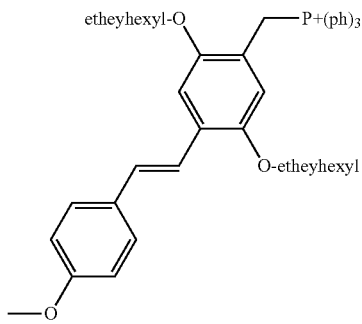

To a solution of 1,4-Di(2'-ethylhexyloxy)-2,5-bis-(triphenylphosphino)methyl]-benzene 230 mg (0.23 mmol) and 4-methoxyaldehyde 31 mg (0.23 mmol) in 10 ml $CH_2Cl_2$ was added dropwise with stirring NaOEt (0.005 g, 0.23 mmol) in 5 ml Ethanol. After 1 hr of stirring the solvent was evaporated in vacuum and was passed through silica gel chromatographic column eluted with dichloromethane:methanol (95:5, v/v) to yield a yellow powder in 50% yield.

NMR: $^1H$ $(CDCl_3)$: 0.55 (t, 6H), 0.82 (m, 16H), 1.07-1.18 (m, 16H), 1.22 (m, 2H), 2.79 (m, 2H), 3.67 (s, 2H), 3.74 (s, 1H), 5.13-5.18 (d, 2H), 6.45 (dd, 2H), 6.61-6.67 (d, 2H), 6.82 (d, 1H), 7.06 (d, 2H), 7.33 (d, 1H), 7.66 (m, 12H), 7.69 (t, 3H). $^{13}C(CDCl_3)$ δ 15.80, 24.8, 25.60, 30.07, 31.0, 32.1, 72.5, 115.9, 119.8, 120.4, 125.4, 129.5, 131.8, 136.1, 136.6, 152.1, 160.4. M.S.: MALDI-TOF [M$^+$-PPh$_3$] m/z 480.33.

5,5'-Bis-(2-{2,5-bis-(2-ethyl-hexyloxy)-4-[2-(4-methoxy-phenyl)-vinyl]-phenyl}-vinyl)-[3,3']bipyridinyl

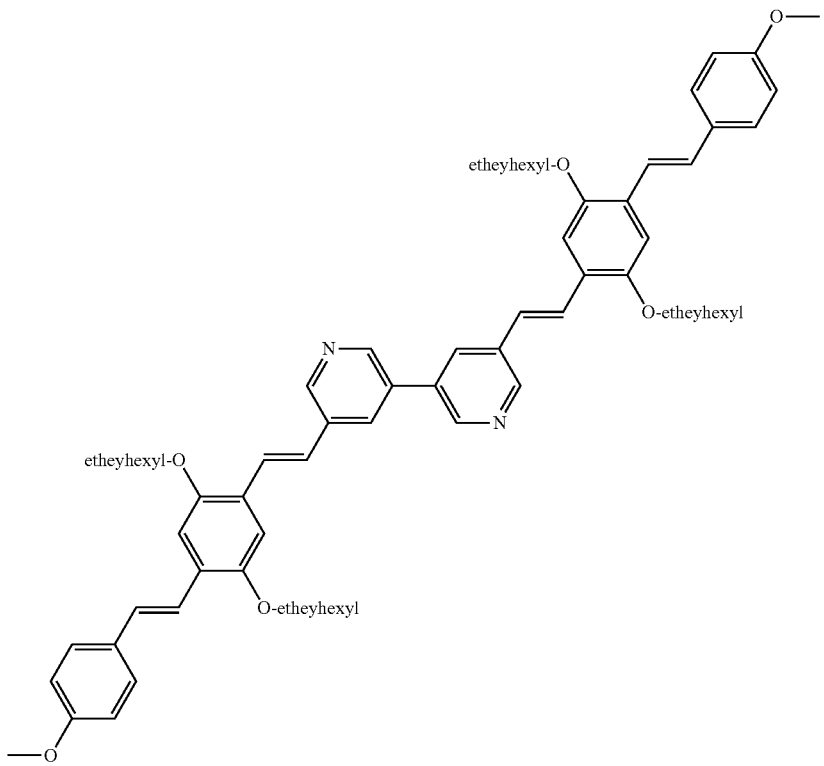

(Chemosensor 8)

To a solution of {2,5-Bis-(2-ethyl-hexyloxy)-4-[2-(4-methoxy-phenyl)-vinyl]-benzyl}-tri phenyl-phosphonium bromide 120 mg (0.15 mmol) and [3,3']-bipyridinyl-5,5'-dicarbaldehyde 15 mg (0.07 mmol) in 10 ml $CH_2Cl_2$ was added NaOEt (0.005 g, 0.23 mmol) in 5 ml Ethanol dropwise with stirring. After 1 hr of stirring the solvent was evaporated in vacuum and was passed through alumina chromatographic column eluted with ethyl acetate:hexane (20:80, v/v) to yield a yellow viscose solid in 80% yield.

NMR: $^1H(CDCl_3)$: 0.88 (t, 12H), 0.93-1.19 (m, 32H), 1.27 (m, 8H), 3.71 (d, 8H), 6.51 (m, 1H), 6.84 (d, 2H), 7.10-7.12 (t, 2H), 7.28 (d, 1H), 7.40-7.43 (d, 2H), 7.60 (m, 2H), 7.50-7.61 (d, 1H), 7.96 (s, 1H), 8.66 (t, 1H), 8.74 (d, 2H) $^{13}C(CDCl_3)$ δ 13.2, 15.9, 24.9, 26.0, 31.0, 31.1, 31.2, 31.5, 32.1, 32.7, 33.7, 41.5, 57.1, 73.2, 111.7, 112.4, 115.3, 115.9, 123.0, 125.6, 125.9, 126.6, 127.0, 128.5, 129.5, 129.9, 130.6, 132.0, 132.5, 132.9, 134.5, 135.8, 148.3, 149.6, 152.7, 153.3, 161.1.

Each of the nine chemosensors was then exposed to the eight alkylating agents one at a time, and the resulting emission level measured. As shown in FIG. 4, the resulting pattern of emission level for each alkylating agent is distinctive and therefore can serve to identify the agent.

Example 5

Identification of Alkylating Agents

As shown in FIG. 5, thirteen chemosensors of the invention (top row) were absorbed on Whatman filter paper. Before exposure to four different alkylating agents (leftmost column) their emission spectra and levels were measured (second from top row) after being excited from a 365 nm light source.

Materials

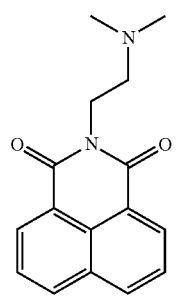

1

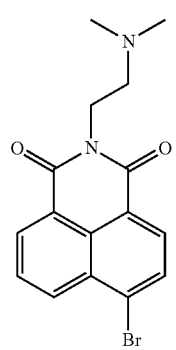

2

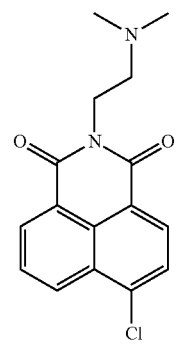

3

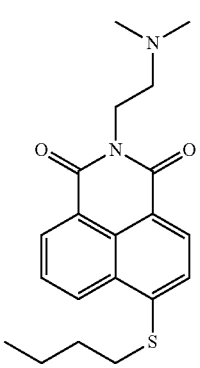

4

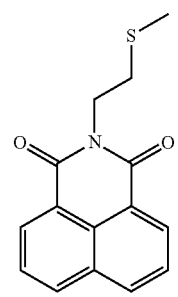

5

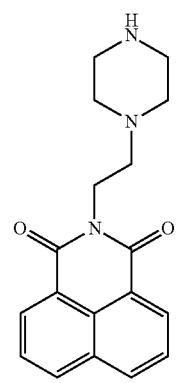

6

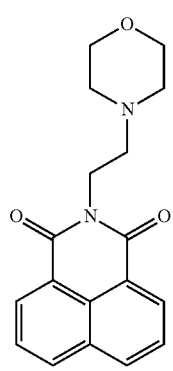
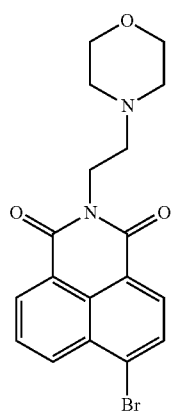
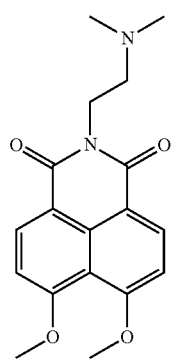
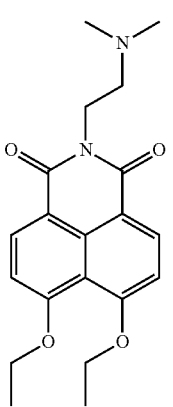
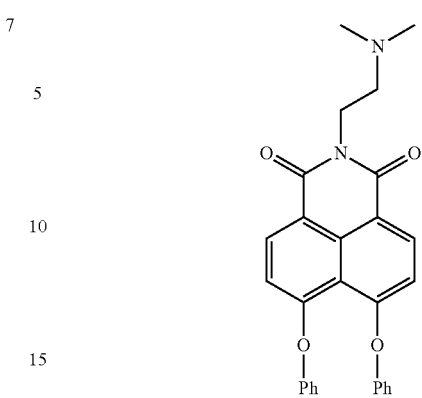
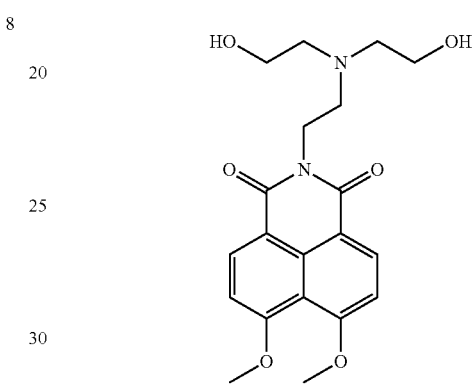
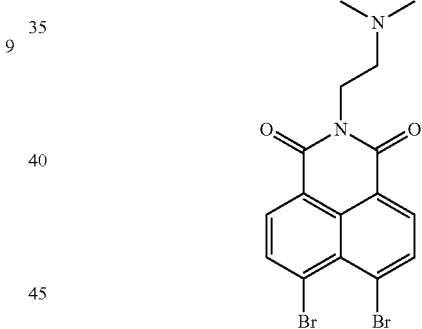
Material 1: S. Claudia et. al. Bioorganic & Medicinal Chemistry (2007), 15(1), 555-562.
Material 2: Y. Peng, Tetrahedron (2005), 61(50), 11895-11901.
Material 3: Zee-Cheng, Journal of Medicinal Chemistry (1985), 28(9), 1216-22.
Material 4:
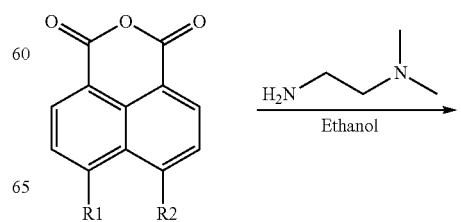

-continued

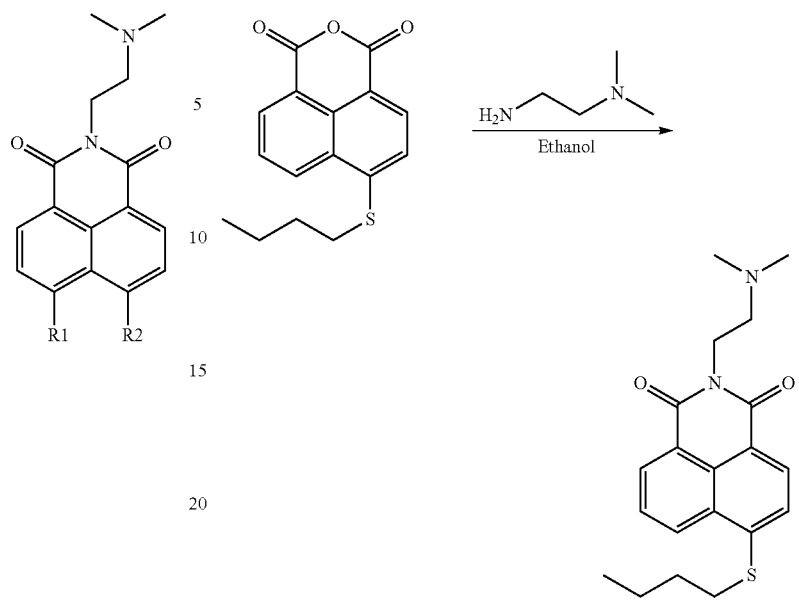

1  R1=R2=H
2  R1=H, R2=Br
3  R1=H, R2=Cl
4  R1=H, R2=SBu
9  R1=OMe, R2=OMe
10 R1=OEt, R2=OEt
11 R1=OPh, R2=OPh
13 R1=Br, R2=Br

General Procedure:

1,8-naphthalic anhydride derivatives (10 mmol) and N,N-dimethylethylenediamine (20 mmol) were added to 10 mL ethanol, the reaction mixture was stirred at reflux temperature for 2 h, then cooled, filtered, and dried, the crude product was obtained as solid. (30-100%).

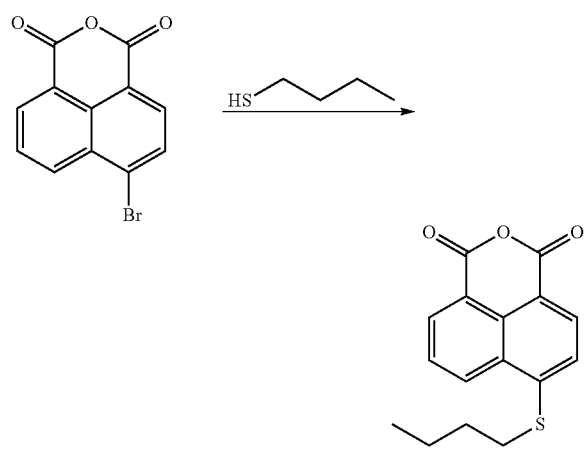

6-Butylsulfanyl-benzo[de]isochromene-1,3-dione 4-bromo-1,8-naphthalic (1 g, 3.6 mmol), 1-butanediol (0.58 gr, 6.4 mmol) and anhydrous $K_2CO_3$ (0.25 gr,) were refluxed for half an hour in dry DMF (10 ml). The mixture was cooled, poured into 25 gram of ice-water and the resulting yellow suspension stirred for 2 hours. The yellow product was filtered, air dried and recrystallised from a mixture of chloroform and petroleum ether to give a product (1 gr, 97%). m/z=287; 1H NMR (ppm) (200 MHz, CDCl$_3$): 1.01 (t, 3H), 1.57 (m, 2H), 1.77 (m, 2H), 3.21 (t, 2H), 7.54 (d, 1H), 7.77 (t, 1H), 8.47 (d, 1H), 8.62 (d, 2H); $^{13}$C NMR (ppm) (500 MHz, CDCl$_3$): 15.4, 23.9, 32, 33.6, 124.1, 128.8, 133.3, 134.7, 135.5.

Material 5: Cho, Dae Won, Journal of Physical Chemistry B (2006), 110(10), 4576-4582.

Material 6: commercially available

Material 7: commercially available

Material 8: Audia, James Edmund; Neubauer, Blake Lee, Eur. Pat. Appl. (1996),

Material 9: Zee-Cheng, Journal of Medicinal Chemistry (1985), 28(9), 1216-22.

Material 10: H. Cao et al. J. Org. Chem. (2005), 70, 4929-4934.

6-Butylsulfanyl-2-(2-dimethylamino-ethyl)-benzo[de]isoquinoline-1,3-dione (XX)

6-Butylsulfanyl-benzo[de]isochromene-1,3-dione (0.16 g, 0.4 mmol) and N,N-dimethylethylenediamine (0.085 ml, 0.8 mmol) were added to 10 mL ethanol, the reaction mixture was stirred at reflux temperature for 2 h, then cooled, filtered, and dried, the crude product was obtained as yellow solid (0.12 g, 90%). m/z=357; $^1$H NMR (ppm) (300 MHz, CDCl$_3$): 1.01 (t, 3H), 1.57 (m, 2H), 1.77 (m, 2H), 2.36 (s, 6H), 2.67 (t, 2H), 3.18 (t, 2H), 4.34 (t, 2H), 7.54 (d, 1H), 7.77 (t, 1H), 8.47 (d, 1H), 8.61 (d, 1H), 8.62 (d, 1H); 13C NMR (ppm) (500 MHz, CDCl$_3$): 15.4, 23.6, 32.2, 33.8, 39.9, 47.5, 58.8, 120.8, 124.5, 124.9, 128.3, 130.2, 131.4, 132, 132.6, 133.3, 147.5, 165.9.

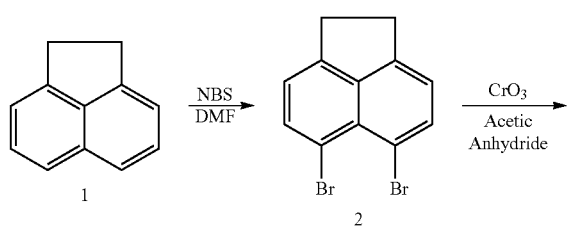

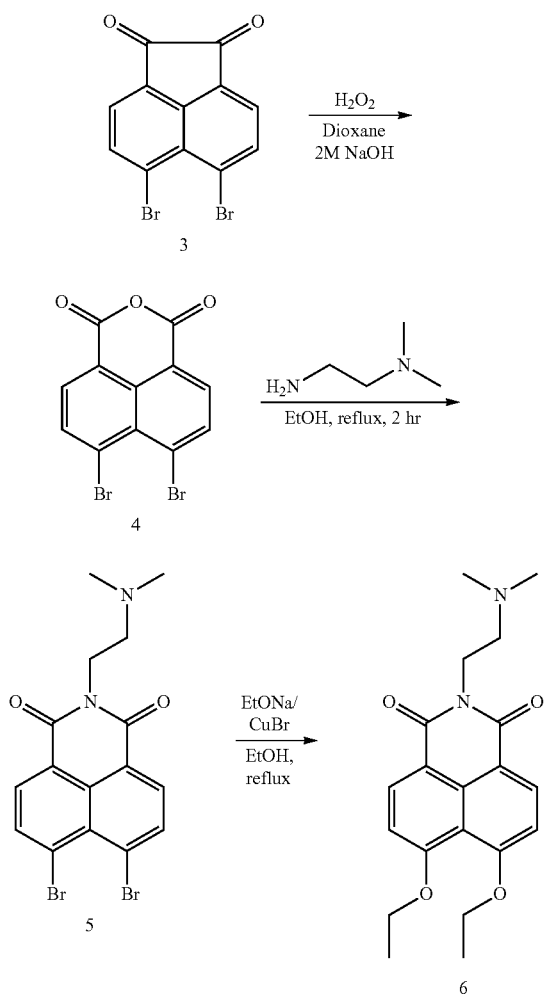

Material 11:

5,6-Dibromoacenaphthene (2)

(W. D. Neudorff et. al., Chem. Eur. J. 2003, 9, 2745-2757). A suspension of N-bromosuccinimide (NBS) (25 gr, 143 mmol) in DMF (50 ml) was added in portions to an ice-cooled suspension of acenaphthene (1) (10 g, 65 mmol) in DMF (15 mL) over a period of 1 h. The temperature of mixture was not allowed exceed 15° C. The mixture was stirred for a further 12 h and then allowed to warm to room temperature. The precipitate was filtered with suction, washed with ethanol (3*50 mL), and purified by stirring over night in refluxing ethanol (200 ml). Cooling to room temperature, filtration, washing with ethanol, and drying in vacuo yielded 4.5 g (22%) of a beige crystalline solid (m.p. 169-172° C.) that was suitable for further work. 1H NMR: 3.28 (s, 4H; H-1,2), 7.06 (d, 3J_7.49 Hz, 2H; H-3,8), 7.76 ppm (d, 3J_7.49 Hz, 2H; H-4,7); 13C NMR (68 MHz, $CDCl_3$): 29.99 (C-1,2), 114.31, 120.87, 131.80, 135.77, 141.75, 147 ppm (arom-C)

1,8-Dibromoacenaphthenedione (3)

(M. Tesmer, H. Vahrenkamp, Eur. J. Inorg. Chem., 2001, 11832-1188). 1,8-Dibromoacenaphthene [2] (8 g, 25.6 mmol) was dissolved in acetic anhydride (0.5 L) at 110° C. $CrO_3$ (20.4 g, 205 mmol) was added carefully to the stirred solution over a period of 2 h. The resulting green suspension was stirred at 160° C. for 30 min., and then poured while hot onto crushed ice (1 kg). Conc. HCl (20 mL) was added and the mixture was filtered. The brownish precipitate was washed with water, dried in vacuo and recrystallized from acetic anhydride (2 L).

1,8-Dibromoacenaphthenedione (6.33 g, 73%) was obtained as a light brown solid, m.p. 239° C. 2 $C_{12}H_4Br_2O_2$ (340.0): calcd. C, 42.40; H, 1.19. found C, 42.22; H, 1.19. 2. 1H NMR ($CDCl_3$): δ 57.93 (d, J 57.6 Hz, 2H, H4,7), 8.27 (d, J 57.6 Hz, 2H, H3,8).

1,8-Dibromonaphthoic Anhydride (4)

(P. Yang et al., Tetrahedron, 2005, 61, 11895-11901). 1,8-Dibromoacenaphthenedione (633 g, 18.6 mmol) was dissolved in a mixture of 1,4-dioxane (400 mL) and NaOH (2 M, 400 mL) and eated to 100° C. A solution of $H_2O_2$ (10%, 400 mL) was added slowly, to the stirred solution. After stirring for a further 30 min. at 100° C., the mixture was cooled to room temp. and filtered. The filtrate was acidified with conc. HCl producing a voluminous precipitate. This was separated by centrifugation, washed twice with water and dried in vacuo. 1,8-dibromonaphthoic anhydride was obtained as a light brown powder, m.p. 260° C. 2 C12H4Br2O3 (356.0): calcd. C, 40.49; H, 1,13. found C, 40.45; H, 1.11. 2 1H NMR ($[D_6]$acetone): ä 5 7.95 (d, J 57.5 Hz, 2H, H5,8), 8.17 (d, J 57.5 Hz, 2H, H4,9).

6,7-Dibromo-2-(2-dimethylamino-ethyl)-benzo[de]isoquinoline-1,3-dione (5)

(H. Cao et al. J. Org. Chem. 2005, 70, 4929-4934). 4,6-dibromo-1,8-naphthalic anhydride (0.86 g, 2.4 mmol) and N,N-dimethylethylenediamine (0.53 ml, 4.8 mmol) were added to 10 mL ethanol, the reaction mixture was stirred at reflux temperature for 2 h, then cooled, filtered, and dried, the crude product was obtained as yellow solid 1 (0.3 g, 30%).

2-(2-Dimethylamino-ethyl)-6,7-diethoxy-benzo[de]isoquinoline-1,3-dione$^i$ (6)

(0.3 gr, 0.7 mmol), 52 mg of CuBr, and a 10:1 stoichiometric ratio of sodium ethoxide in 20 ml ethanol, sodium (0.164 gr, 7 mmol) were stirred and refluxed for 18 h. Ethanol was removed by distillation. Crude product was purified by silica gel. The reaction afforded a tan or yellow powder (0.27 gr, 100%).

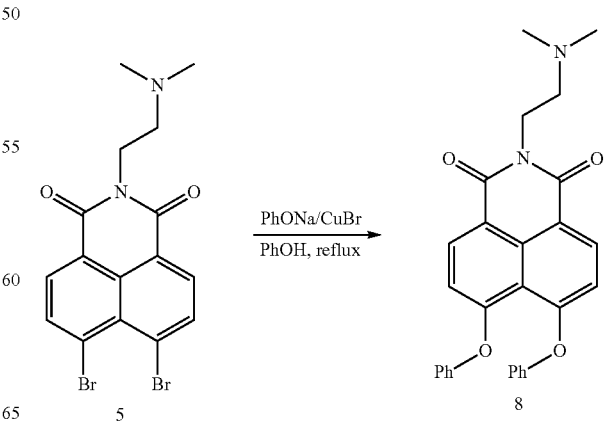

Material 12:

2-(2-Dimethylamino-ethyl)-6,7-diphenoxy-benzo[de]isoquinoline-1,3-dione (8)

(0.07 gr, 0.017 mmol), 10 mg of CuBr, and a 10:1 stoichiometric ratio of sodium methoxide in 20 ml methanol, sodium (0.038 gr, 0.17 mmol) were stirred and refluxed for 18 h. Methanol was removed by distillation. Crude product was purified by silica gel. The reaction afforded a brown powder (0.04 gr, 55%). m/z=453; 1H NMR (ppm) (300 MHz, CDCl$_3$): 1.56 (s, 6H), 2.6 (t, 2H), 4.26 (t, 2H), 6.8 (d, 4H), 6.97 (d, 2H), 7.09 (t, 2H), 7.27 (t, 4H), 8.49 (d, 2H).

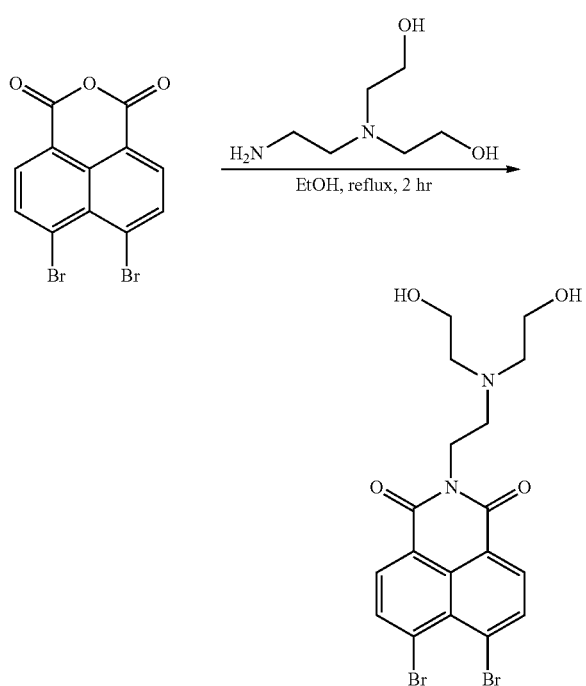

4-Bromo-1,8-naphthalic anhydride (0.3 g, 0.85 mmol) and N,N-Bis(2-hydroxyethyl)ethylenediamine (0.13 ml, 0.93 mmol) were added to ethanol (15 ml) and refluxed for 6 h. The solution was then cooled to precipitate the desired product (0.11 g, 27%) as a white solid. m/z=486; 1H NMR (ppm) (300 MHz, CDCl$_3$): 2.68 (t, 4H), 2.89 (t, 2H), 3.46 (t, 4H), 4.24 (t, 2H), 8.17 (d, 2H), 8.39 (d, 2H).

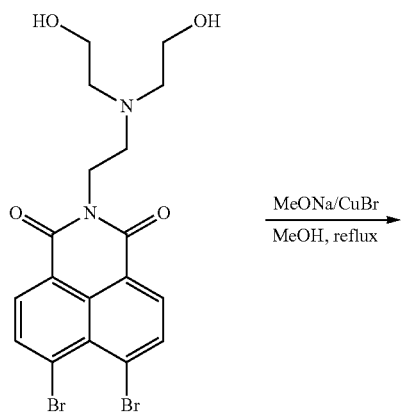

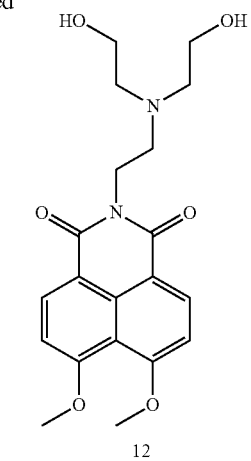

2-{2-[Bis-(2-hydroxy-ethyl)-amino]ethyl}-6,7-dimethoxy-benzo[de]isoquinoline-1,3-dione (12)

(0.11 gr, 0.22 mmol), 10 mg of CuBr, and a 10:1 stoichiometric ratio of sodium methoxide in 20 ml methanol, sodium (0.104 gr, 2.2 mmol) were stirred and refluxed for 18 h. Methanol was removed by distillation. Crude product was purified by silica gel. The reaction afforded a yellow powder (0.066 gr, 77%). m/z=388; 1H NMR (ppm) (300 MHz, CDCl$_3$): 2.68 (t, 4H), 2.89 (t, 2H), 3.46 (t, 4H), 4.23 (t, 2H), 7.05 (d, 2H), 8.55 (d, 2H).

Material 13: see FIG. 3 and Example 3

Each of the thirteen chemosensors was then exposed to the four alkylating agents one at a time, and the resulting emission level measured. As shown in FIG. 5, the resulting pattern of emission level for each alkylating agent is distinctive and therefore can serve to identify the agent.

All references cited herein are incorporated in their entirety. It is appreciated that the detailed description above is intended only to illustrate certain preferred embodiments of the present invention. It is in no way intended to limit the scope of the invention, as set out in the claims.

We claim:

1. A method for identifying a test molecule in a sample, said test molecule comprising an electrophilic or nucleophilic moiety, comprising:
   a) contacting said sample with a plurality of chemosensor molecules, each of said chemosensor molecules comprising a π-conjugated system and a moiety having a nucleophilic property or an electrophilic property, thereby reacting said plurality of said chemosensor molecules with said test molecule, and forming conjugate molecules, said conjugate molecules having a structure determined at least partially according to a structure of said test molecule; and
   b) measuring an electromagnetic property of said conjugate molecules in the sample; whereby the pattern of changes in the electromagnetic properties of the plurality of conjugate molecules after chemically reacting with said electrophilic or nucleophilic moiety of each test molecule identifies said test molecule in said sample; wherein said electromagnetic properties are selected from the group consisting of conduction, induction and dielectric property.

2. The method of claim 1, wherein the test molecule is identified within a sample of a quantifiable of unknown molecules.

3. The method of claim 2, wherein the quantifiable number of unknown molecules is 100 or less.

4. The method of claim 2, wherein the quantifiable number of unknown molecules is 50 or less.

5. The method of claim 2, wherein the quantifiable number of unknown molecules is 20 or less.

6. The method of claim 1, wherein at least one of said chemosensor molecules chemically reacts with said electrophile of said test molecule.

7. The method of claim 1, wherein at least one of said chemosensor molecules chemically reacts with said nucleophile of said test molecule.

8. The method of claim 1, wherein the electromagnetic property measured is the photo-induced electron transfer (PET) or energy transfer between the re-conjugated moiety and the nucleophilic moiety.

9. The method of claim 1, wherein the electromagnetic property measured is derived from a change in the electron density of the highest occupied molecular orbital (HOMO) or lowest unoccupied molecular orbital (LUMO) or the change in the location of the HOMO or LUMO.

10. The method of claim 1, wherein at least one chemosensor molecule has the formula A-B, wherein A comprises a π-conjugated system, and B comprises a nucleophilic or electrophilic moiety.

11. The method of claim 1, wherein at least one chemosensor molecule has a) the π-conjugated property and b) the nucleophilic or electrophilic property in one moiety.

12. The method of claim 10, wherein A and B are π-conjugated to each other.

13. The method of claim 1, wherein at least one chemosensor molecule comprises an aromatic or heteroaromatic moiety having a pendant nucleophile.

14. The method of claim 1, wherein at least one chemosensor molecule comprises an aromatic or heteroaromatic moiety having a pendant electrophile or nucleophile.

15. The method of claim 1, wherein at least one chemosensor molecule is an oligomer or polymer.

16. The method of claim 15, wherein said oligomer or polymer has the structure A-B, wherein A comprises a π-conjugated moiety and B comprises at least one nucleophilic moiety and A and B are connected to each other via π-conjugation.

17. The method of claim 16, wherein said oligomer or polymer comprises a) repeating π-conjugated units (A), each being π-conjugated with the adjacent group; and b) and nucleophilic groups (B), each nucleophilic group being a pendant side group that is π-conjugated with a π-conjugated unit of A.

18. The method of claim 1, wherein test molecule in said sample is inorganic.

19. The method of claim 1, wherein test molecule in said sample is organic.

20. The method of claim 1, wherein test molecule in said sample contains an electrophile.

21. The method of claim 1, wherein test molecule in said sample contains a nucleophile.

22. The method of claim 20, wherein test molecule is an alkylating agent.

23. The method of claim 1, wherein said sample is taken from the atmosphere.

24. The method of claim 1, wherein said sample is biological in origin.

25. The method of claim 1, wherein said sample contains two or more different test molecules.

26. The method of claim 1, wherein said chemosensor molecules are in solution.

27. The method of claim 1, wherein said chemosensor molecules are immobilized on a solid or semi-solid support.

28. The method of claim 1, wherein said chemosensor molecules are in a gel or a matrix.

29. The method of claim 27, wherein said solid support is selected from a bead or particle, a microsphere, a nanobead, glass, a flexible membrane, a semi-rigid or rigid membrane, a plastic, a metal, and a mineral surface.

30. A device for the identification of an electrophile or nucleophile, said device comprising a substrate carrying a plurality of chemosensor molecules having at least one predetermined electromagnetic property, said at least one electromagnetic property being changeable by subjecting the chemosensor molecules to a sample containing at least one electrophile or nucleophile, wherein the pattern of change of said electromagnetic property of said plurality of chemosensor molecules allows the device to identify said electrophile or nucleophile in said sample; wherein said electromagnetic property is selected from the group consisting of conduction, induction and dielectric property.

31. The method of claim 1, wherein said plurality of chemosensor molecules have at least two different molecular structures.

32. The method of claim 1, wherein said plurality of chemosensor molecules have the same molecular structure.

33. A method for identifying a test molecule in a sample, said test molecule comprising an electrophilic or nucleophilic moiety, comprising:
    a) contacting said sample with a plurality of chemosensor molecules, each of said chemosensor molecules comprising a π-conjugated system and a moiety having a nucleophilic property or an electrophilic property;
    b) forming conjugate molecules according to a reaction of said plurality of said chemosensor molecules with said test molecule; and
    c) measuring an electromagnetic property of said conjugate molecules in the sample; whereby the pattern of changes in the electromagnetic properties of the plurality of conjugate molecules after chemically reacting with said electrophile or nucleophile of each test molecule identifies said test molecule in said sample; wherein said electromagnetic properties are selected from the group consisting of conduction, induction and dielectric property.

34. A method for detecting or identifying a test molecule in a sample, said test molecule comprising an electrophilic or nucleophilic moiety, comprising:
    a) contacting said sample with a plurality of chemosensor molecules, each of said chemosensor molecules comprising a π-conjugated system and a moiety having a nucleophilic property or an electrophilic property;
    b) if said plurality of said chemosensor molecules chemically reacts with said test molecule, forming conjugate molecules, said conjugate molecules having a structure determined at least partially according to a structure of said test molecule, wherein said test molecule is an alkylator, such that said conjugate molecule is formed through alkylation; and
    c) measuring an electromagnetic property of said conjugate molecules in the sample; whereby the pattern of changes in the electromagnetic properties of the plurality of conjugate molecules after chemically reacting with said electrophile or nucleophile of each test molecule identifies said test molecule in said sample; wherein said electromagnetic properties are selected from the group consisting of optical, conduction, induction and dielectric property.

35. The method of claim 34, wherein the electromagnetic property measured is the luminescence and/or color difference between the chemosensor and the reacted chemosensor.

36. The method of claim 10, wherein A and B are not π-conjugated to each other.

* * * * *